United States Patent
Gupta et al.

(10) Patent No.: US 6,239,276 B1
(45) Date of Patent: May 29, 2001

(54) NON-YELLOWING PARA-TERTIARY-ALKYL PHENYL SUBSTITUTED TRIAZINE AND PYRIMIDINE ULTRAVIOLET LIGHT ABSORBERS

(75) Inventors: Ram B. Gupta, Stamford; Dennis J. Jakiela, Orange, both of CT (US)

(73) Assignee: Cytec Technology Corporation, Wilmington, DE (US)

( * ) Notice: Subject to any disclaimer, the term of this patent is extended or adjusted under 35 U.S.C. 154(b) by 0 days.

(21) Appl. No.: 09/335,885

(22) Filed: Jun. 18, 1999

Related U.S. Application Data

(60) Provisional application No. 60/108,895, filed on Nov. 17, 1998, and provisional application No. 60/090,247, filed on Jun. 22, 1998.

(51) Int. Cl.⁷ .................................................. C07D 251/24
(52) U.S. Cl. .......................... 544/213; 544/214; 544/215
(58) Field of Search .................................. 544/213, 214, 544/215

(56) References Cited

U.S. PATENT DOCUMENTS

| | | | |
|---|---|---|---|
| 3,043,709 | 7/1962 | Amborski | 117/7 |
| 3,118,837 | 1/1964 | Briggs | 210/232 |
| 3,242,175 | 3/1966 | Duennenberger et al. | 544/213 |
| 3,244,708 | 4/1966 | Duennenberger et al. | 544/215 |
| 3,309,220 | 3/1967 | Osteen | 544/213 |
| 3,423,360 | 1/1969 | Huber et al. | 549/213 |
| 3,487,505 | 1/1970 | Chisholm et al. | 18/13 |
| 3,557,265 | 1/1971 | Chisholm et al. | 264/47 |
| 3,843,371 | 10/1974 | Piller et al. | 544/213 |
| 3,896,125 | 7/1975 | Helmo et al. | 260/249.5 |
| 4,161,592 | 7/1979 | Evans et al. | 544/198 |
| 4,314,933 | 2/1982 | Berner | 260/45.75 N |
| 4,325,863 | 4/1982 | Hinsken et al. | 624/111 |
| 4,338,244 | 7/1982 | Hinsken et al. | 524/109 |
| 4,344,876 | 8/1982 | Berner | 524/91 |
| 4,353,965 | 10/1982 | Olson et al. | 428/412 |
| 4,426,471 | 1/1984 | Berner | 524/91 |
| 4,426,472 | 1/1984 | Berner | 524/99 |
| 4,481,664 | 11/1984 | Linger et al. | 382/8 |
| 4,518,686 | 5/1985 | Sasaki et al. | 430/512 |
| 4,540,623 | 9/1985 | Im et al. | 428/220 |
| 4,619,956 | 10/1986 | Susi | 524/87 |
| 4,668,588 | 5/1987 | Kishima | 428/412 |
| 4,740,542 | 4/1988 | Susi | 524/87 |
| 4,775,707 | 10/1988 | Slongo et al. | 524/91 |
| 4,826,978 | 5/1989 | Migdal et al. | 544/216 |
| 4,853,471 | 8/1989 | Rody et al. | 548/261 |
| 4,921,966 | 5/1990 | Stegmann et al. | 548/260 |
| 4,937,026 | 6/1990 | Goossens et al. | 264/129 |
| 4,948,666 | 8/1990 | Paul et al. | 428/334 |
| 4,960,863 | 10/1990 | Rosenquist | 528/480 |
| 4,962,142 | 10/1990 | Migdal et al. | 524/100 |
| 4,973,701 | 11/1990 | Winter et al. | 548/260 |
| 4,973,702 | 11/1990 | Rody et al. | 548/261 |
| 4,992,322 | 2/1991 | Curry et al. | 428/215 |
| 5,004,770 | 4/1991 | Cortolano et al. | 524/99 |
| 5,006,577 | 4/1991 | Behrens et al. | 524/95 |
| 5,030,731 | 7/1991 | Slongo et al. | 548/260 |
| 5,064,883 | 11/1991 | Behrens et al. | 524/95 |
| 5,071,981 | 12/1991 | Son et al. | 544/198 |
| 5,106,891 | 4/1992 | Valet | 524/91 |
| 5,106,972 | 4/1992 | Burdeska et al. | 544/219 |
| 5,112,890 | 5/1992 | Behrens et al. | 524/95 |
| 5,124,378 | 6/1992 | Behrens et al. | 524/95 |
| 5,175,312 | 12/1992 | Dubs et al. | 549/307 |
| 5,189,084 | 2/1993 | Birbaum et al. | 524/100 |
| 5,198,498 | 3/1993 | Valet et al. | 525/125 |
| 5,204,473 | 4/1993 | Winter et al. | 546/188 |
| 5,216,052 | 6/1993 | Nesvadba et al. | 524/108 |
| 5,252,643 | 10/1993 | Nesvadba | 524/111 |
| 5,288,788 | 2/1994 | Shieh et al. | 524/495 |
| 5,298,067 | 3/1994 | Valet et al. | 106/506 |
| 5,322,868 | 6/1994 | Valet et al. | 524/89 |
| 5,354,794 | 10/1994 | Stevenson et al. | 524/100 |
| 5,356,995 | 10/1994 | Valet et al. | 525/100 |
| 5,369,140 | 11/1994 | Valet et al. | 522/75 |
| 5,376,710 | 12/1994 | Slongo et al. | 524/87 |
| 5,420,204 | 5/1995 | Valet et al. | 525/125 |
| 5,438,138 | 8/1995 | Henneberger et al. | 544/217 |
| 5,445,872 | 8/1995 | Suhadolnik et al. | 428/215 |
| 5,459,222 | 10/1995 | Rodgers et al. | 528/73 |

(List continued on next page.)

FOREIGN PATENT DOCUMENTS

| | | |
|---|---|---|
| 3922496 | 1/1991 | (DE) . |
| 4316611 | 11/1993 | (DE) . |
| 4316622 | 11/1993 | (DE) . |
| 4316876 | 11/1993 | (DE) . |

(List continued on next page.)

OTHER PUBLICATIONS

Brunetti, H.; Luethi, C. E. *Helv. Chimica, Acta,* 55, (1972) 1566–1595.

Tanimoto, S.; Yamagata, M., *Senryo to Yakahin,* 40, (1995) 339ff.

(List continued on next page.)

*Primary Examiner*—Mukund J. Shah
*Assistant Examiner*—Venkataraman Balasubramanian
(74) *Attorney, Agent, or Firm*—Pennie & Edmonds LLP

(57) ABSTRACT

This invention relates generally to para-tertiary alkyl phenyl substituted pyrimidines and triazines and the use thereof to protect against degradation by environmental forces, inclusive of ultraviolet light, actinic radiation, oxidation, moisture, atmospheric pollutants and combinations thereof. The new class of para-tertiary alkyl phenyl substituted pyrimidines and triazines includes two tertiary alkylated phenyl groups, and a resorcinol or substituted resocinol group attached to the triazine or pyrimidine ring. These materials may, under the appropriate circumstances, be bonded to formulations comprising coatings, polymers, resins, organic compounds and the like via reaction of the bondable functionality with the materials of the formulation. A method for stabilizing a material by incorporating such para-tertiary alkyl phenyl substituted pyrimidines and triazines is also disclosed.

10 Claims, No Drawings

U.S. PATENT DOCUMENTS

| | | | |
|---|---|---|---|
| 5,461,151 | 10/1995 | Waterman | 544/216 |
| 5,476,937 | 12/1995 | Stevenson et al. | 544/216 |
| 5,478,935 | 12/1995 | Reinehr et al. | 544/180 |
| 5,563,224 | 10/1996 | Szita et al. | 525/480 |
| 5,585,422 | 12/1996 | Falk et al. | 524/100 |
| 5,597,854 | 1/1997 | Birbaum et al. | 524/100 |
| 5,637,706 | 6/1997 | Stevenson et al. | 544/216 |
| 5,726,309 | 3/1998 | Stevenson et al. | 544/216 |

FOREIGN PATENT DOCUMENTS

| | | |
|---|---|---|
| 309400 | 3/1989 | (EP) . |
| 309401 | 3/1989 | (EP) . |
| 309402 | 3/1989 | (EP) . |
| 434608 | 6/1991 | (EP) . |
| 444323 | 9/1991 | (EP) . |
| 520938 | 12/1992 | (EP) . |
| 531258 | 3/1993 | (EP) . |
| 577559 | 1/1994 | (EP) . |
| 589839 | 3/1994 | (EP) . |
| 591102 | 4/1994 | (EP) . |
| 648756 | 4/1995 | (EP) . |
| 649841 | 4/1995 | (EP) . |
| 704437 | 3/1996 | (EP) . |
| 779280 A1 | 6/1997 | (EP) . |
| 2269819 | 2/1994 | (GB) . |
| 2290745 A0 | 1/1996 | (GB) . |
| 2293823 | 4/1996 | (GB) . |
| WO 94/04515 | 3/1994 | (WO) . |
| WO 96/28431 | 9/1996 | (WO) . |

OTHER PUBLICATIONS

Ullmann's Encyclopedia of Industrial Chemistry, $5^{th}$ Edition, vol. A18, pp. 368–426 VCH Verlagsgesellschaft, Weinheim 1991 pp. 429–471, 491–500.

Calbo, Leonard J., ed., Handbook of Coatings Additives, New York: Marcel Dekker (1987).

Diffey, B. L.; Robson, J., *J. Soc. Cosmet, Chem.*, 40, (1989) 127–133.

NON-YELLOWING PARA-TERTIARY-ALKYL PHENYL SUBSTITUTED TRIAZINE AND PYRIMIDINE ULTRAVIOLET LIGHT ABSORBERS

This application claims benefit from U.S. Provisional application No. 60/090,247 filed Jun. 22, 1998 and Ser. No. 60/108,825 filed on Apr. 17, 1998.

BACKGROUND OF THE INVENTION

This invention relates generally to novel para-tertiary alkyl phenyl substituted triazines and pyrimidines and their use as protectants against degradation by environmental forces, including ultraviolet light, actinic radiation, oxygen, moisture, atmospheric pollutants and combinations thereof.

Exposure to sunlight and other sources of ultraviolet radiation is known to cause degradation of a variety of materials, especially polymeric materials. For example, polymeric materials such as plastics often discolor and may become brittle as a result of exposure to ultraviolet light. Accordingly, a large body of art has been developed directed towards materials such as ultraviolet light absorbers and stabilizers which are capable of inhibiting such degradation.

A class of materials known to be ultraviolet light absorbers are o-hydroxyphenyltriazines, in which at least one substituent on the 1, 3 or 5 carbon on the triazine ring is a phenyl group with a hydroxyl group ortho to the point of attachment to the triazine ring. In general this class of materials is well known in the art. Disclosures of such compounds can be found in U.S. Pat. No. 3,242,175 and U.S. Pat. No. 3,244,708.

A further example is found in U.S. Pat. Nos. 3,843,371 and 3,896,125, which disclose various hydroxyphenyltriazines. These triazines show poor solubilities and poor stabilities, and can discolor with time.

Hydroxyphenyltriazines in combination with other UV absorbers such as hydroxyphenylbenzotriazoles, benzophenones, oxanilides, cyanoacrylates, salicylates, acrylonitriles and thiozlines, are also well known. For example, U.S. Pat. Nos. 4,853,471, 4,973,702, 4,921,966 and 4,973,701 disclose such combinations.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para- to the point of attachment to the triazine ring. For example, U.S. Pat. Nos. 3,118,837 and 3,244,708 disclose p-alkoxy-o-hydroxyphenyl triazines with improved UV protection, but such triazines also exhibit poor solubility and poor long-term stabilities.

This para-substituent can be "non-reactive," as in the case of an alkyloxy group, or "reactive" as in the case of a hydroxyalkyloxy (active hydrogen reactive site) or (meth) acryloyl (ethylenic unsaturation reactive site) group. For the purposes of the present invention, the former are referred to as "non-bondable" benzocycle-substituted pyrimidines and triazines and the latter are referred to as "bondable" para-tertiary alkyl phenyl substituted pyrimidines and triazines.

Many polymer additives (such as ultraviolet light stabilizers) volatilize or migrate out of the polymer substrate to be protected, or are adsorbed (chemically or physically) by one or more systems components (such as pigments), thereby diminishing their effectiveness. Such volatilization, migration and adsorption problems are examples of the general problems of lack of solubility and compatibility found for many commercial polymer additives. Bondable triazines are well known in the art. For example, U.S. Pat. Nos. 3,423,360, 4,962,142 and 5,189,084 disclose various bondable and the incorporation of these compounds into polymers by chemical bonding. Bondable stabilizers have a potential advantage in this respect in that, depending on the bondable functionality and the particular polymer system to be stabilized, they can be chemically incorporated into a polymer structure via reaction of the bondable functionality either during polymer formation (such as in the case of polymerizing monomers or a crosslinking polymer system) or subsequently with a preformed polymer having appropriate reactive functionality. Due to such bonding, migration of these UV absorbers between layers of multi-layer coatings and into polymer substrates is greatly reduced.

Several of the previously incorporated references disclose tertiary alkylated substituted triazines. For example U.S. Pat. No. 3,242,175 and U.S. Pat. No. 3,244,708 disclose mono-tertiary butylated benzene triazines. There remains a need for new UV-stabilizers which possess improved compatibility with the polymer systems to which they are added, as well as impart improved environmental stability to such systems. The present invention provides novel para-tertiary alkyl phenyl substituted triazine and pyrimidine stabilizers which satisfy this need.

SUMMARY OF THE INVENTION

The present invention provides a new class of para-tertiary alkyl phenyl-substituted pyrimidines and triazines depicted below, in which a substituent attached to the triazine or pyrimidine ring is a bondable or non-bondable para-tertiary alkyl phenyl group:

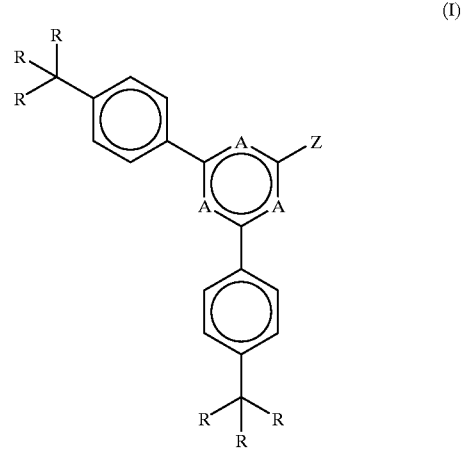

(I)

wherein Z signifies a resorcinol radical which is bound through a cyclic carbon atom directly to the triazine ring or a substituted resorcinol radical, A can be a nitrogen or optionally substituted methine, and each R signifies a hydrocarbyl group to form a tertiary carbon attached to the ring. These para-tertiary alkyl phenyl substituted triazines and pyrimidines have the advantage of being highly soluble in and compatible with many polymers and coatings while being stable to environmental degradation that has lead previous UV stabilizers to turn yellow and to degrade with respect to performance as UV absorbers.

More specifically, the new para-tertiary alkyl phenyl substituted pyrimidines and triazines of the present invention have general formula (II):

(II)

[Chemical structure diagram showing a central ring with A positions, substituted with phenyl groups bearing R substituents and a phenyl group with XO, OL, R³, R⁴ substituents]

wherein
- each A is independently nitrogen or methine optionally substituted with R², and at least two A are nitrogen;
- X is independently selected from hydrogen and a blocking group
- each of L, R³ and R⁴ are independently a hydrogen, hydrocarbyl, halogen, hydroxyl, cyano, —O(hydrocarbyl), —O(functional hydrocarbyl), —N(hydrocarbyl)(hydrocarbyl), —N(functional hydrocarbyl)(functional hydrocarbyl), —S(hydrocarbyl), —S(functional hydrocarbyl), —SO₂ (hydrocarbyl), —SO₃(hydrocarbyl), —SO₂(functional hydrocarbyl), —SO₃(functional hydrocarbyl), —COO (hydrocarbyl), —COO(functional hydrocarbyl), —CO (hydrocarbyl), —CO(functional hydrocarbyl), —OCO (hydrocarbyl), —OCO(functional hydrocarbyl), —CONH₂, —CONH(hydrocarbyl), —CONH (functional hydrocarbyl), —CON (hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups; and
- each R is identical or different, and is independently a hydrocarbyl group of between 1 and 21 carbon atoms, an alkenyl group of between 2 and 21 atoms, a cycloalkyl of between 5 and 21 carbon atoms, an aralkyl of between 7 and 21 carbon atoms, and of the above hydrocarbyl groups substituted with one or more groups selected from the following:
  halogen, hydroxyl, cyano, —O(hydrocarbyl), —O(functional hydrocarbyl), —N(hydrocarbyl)(hydrocarbyl), —N(functional hydrocarbyl)(functional hydrocarbyl), —S(hydrocarbyl), —S(functional hydrocarbyl), —SO₂(hydrocarbyl), —SO₃ (hydrocarbyl), —SO₂(functional hydrocarbyl), —SO₃ (functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH₂, —CONH (hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl); provided that the R groups are connected to a quaternary carbon that is attached to the ring.

Preferably L is hydrogen, a hydrocarbyl group of 1 to 24 carbon atoms, or a functional hydrocarbyl group of 1 to 24 carbon atoms; and R is methyl, ethyl, propyl or phenyl. It is more preferred that each tertiary carbon attached to the ring have two R groups of methyl, ethyl or propyl and one of phenyl, or all three R groups being methyl, ethyl or propyl. It is most preferred for each tertiary carbon to have two R groups being methyl with the third R group being alkyl or phenyl. More preferably, each L in formula (II) is independently selected from the group consisting of:

hydrogen; an alkyl of 1 to 24 carbon atoms optionally substituted by one or more hydroxyl, alkoxy, carboxy, carboalkoxy, amino, amido, carbamato, or epoxy groups, and which may contain one or more carbonyl groups, oxygen atoms or nitrogen atoms in the chain;

an alkenyl of 2 to 24 carbon atoms optionally substituted by hydroxyl, alkoxy, carboxy, carboalkoxy, amino, amido, carbamato, or epoxy groups and which may contain one or more carbonyl groups, oxygen atoms or nitrogen atoms in the chain;

an aralkyl of 7 to 24 carbon atoms optionally substituted by one or more hydroxyl, alkoxy, chloro, cyano, carboxy, carboalkoxy, amino, amido, carbamato, or epoxy groups and may contain one or more carbonyl groups, oxygen atoms or nitrogen atoms in the ring;

a polyoxyalkylene radical of the formula XII $$-CH_2-CH(OH)-CH_2-O-(CH_2-(CH_2)_u-O-)_{mm}-D_1 \quad (XII)$$

wherein $D_1$ is hydrogen, $$-CH_2-CH\underset{O}{\overset{}{\diagdown\diagup}}CH_2$$

$-CH_2-CH(OH)-CH_2-OH$, or $R^{25}$;

a polyoxyalkylene radical of the formula XIII $$-CO-(CH_2)_u-O-(CH_2-(CH_2)_u-O-)_{mm}-D_2 \quad (XIII)$$

wherein $D_2$ is $-(CH_2)-CO-R^{22}$ or $R^{25}$;

a polyoxyalkylene radical of the formula VIII $$-YY-O-CO-(CH_2)_u-O-(CH_2-(CH_2)_u-O-)_{mm}D_3 \quad (XIV)$$

wherein $D_3$ is $-(CH_2)_u-CO-R^{22}$ or $R^{25}$;

a polyoxyalkylene radical of the formula XV $$-(CH_2)_{kk}-CH(R^{21})-CO-B_1-(C_{nn}H_{2nn}-O-)_{mm}-C_{nn}H_{2nn}-B_1-D_4 \quad (XV)$$

wherein $D_4$ is hydrogen of $R^{25}$;

a polyoxyalkylene radical of the formula XVI $$-CO-CH_2-CH_2-NH-(C_{nn}H_{2nn}-O-)_{mm}-C_{nn}H_{2nn}-D_5 \quad (XVI)$$

wherein $D_5$ is $-NH_2$, $-NH-(CH_2)_2-COO-R^{23}$ or $-O-R^{25}$;

a polyoxyalkylene radical of the formula XVII $$-YY-O-CO-CH_2-CH_2-NH-(C_{nn}H_{2nn}-O-)_{mm}-C_{nn}H_{2nn}-D_5 \quad (XVII)$$

wherein $D_5$ is as defined under formula (XVI);
a polyoxyalkylene radical of the formula XVIII $$-(C_{nn}H_{2nn}-O-)_{mm}-C_{nn}H_{2nn}-D_6 \quad (XVIII)$$

wherein $D_6$ is —NH—CO—$R^{24}$, —$OR^{25}$, OH or H;
a polyoxyalkylene radical of the formula XIX (XIX)

$$—\underset{\underset{R^{17}}{|}}{CH}—CH_2—(O\underset{\underset{R^{17}}{|}}{CH}—CH_2)_m—D_7 \qquad (XIX)$$

wherein $D_7$ is —$OR^{25}$, —$NHCOR^{24}$ or —$OCH_2CH_2OR^{25}$;
$R^{21}$ is hydrogen or $C_1$–$C_{16}$ alkyl;
$R^{22}$ is halogen or —O—$R^{23}$;
$R^{23}$ is hydrogen, $C_1$–$C_6$ alkyl, $C_3$–$C_6$ alkenyl, aryl, or aryl-$C_1$–$C_4$-alkyl;
$R^{24}$ is hydrogen, $C_1$–$C_{12}$ alkyl or aryl;
$R^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl;
$R^{26}$ is hydrogen or $C_1$–$C_4$ alkyl;
$R^{27}$ is hydrogen, $C_1$–$C_{18}$ alkyl, $C_3$–$C_6$ alkenyl, $C_1$–$C_{18}$ alkoxy, halogen or aryl-$C_1$–$C_4$-alkyl;
$R^{28}$ and $R^{29}$ independently of one another are hydrogen, $C_1$–$C_{18}$ alkyl, $C_3$–$C_6$ alkenyl, $C_1$–$C_{18}$ alkoxy, or halogen;
$R^{30}$ is hydrogen, $C_1$–$C_4$ alkyl or CN;
YY is unsubstituted or substituted $C_2$–$C_{20}$ alkyl;
$B_1$ is HN or O;
kk is zero or an integer from 1–16;
mm is an integer from 2 to 60;
nn is an integer from 2 to 6;
u is an integer from 1 to 4;
and R is methyl.

The para-tertiary alkyl phenyl substituted pyrimidines and triazines of the present invention further comprise oligomeric species of formulas (III), (IV) and (V):

(III)

wherein
A, R, $R^3$, $R^4$, and X, are as defined above;
r is an integer between 2 and 4;
D when r is 2, is selected from the group consisting of $C_2$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$–$C_{20}$ alkyl which is interrupted by one or more oxygen atoms, —$CH_2CH(OH)CH_2O$—$R^{15}$—$OCH_2CH(OH)CH_2$—, —CO—$R^{16}$—CO—, —CO—NH—$R^{17}$—NH—CO—, —$(CH_2)_s$—COO—$R^{18}$—OCO—$(CH_2)_s$— a polyoxyalkylene bridge member of the formula XX $$—CH_2—CH(OH)—CH_2—O—(CH_2—(CH_2)_u—O—)_{mm}—CH_2—CH(OH)—CH_2— \qquad (XX),$$

a polyoxyalkylene bridge member of the formula XXI $$—CO—(CH_2)_u—O—(CH_2—(CH_2)_u—O—)_{mm}—(CH_2)_u—CO— \qquad (XXI),$$

a polyoxyalkylene bridge member of the formula XXII $$—YY—O—CO(CH_2)_u—O—(CH_2—(CH_2)_u—O—)_{mm}—(CH_2)_u—COO—YY— \qquad (XXII),$$

a polyoxyalkylene bridge member of the formula XXIII $$—(CH_2)_{kk}—CH(R^{21})—CO—B_1—(C_{nn}H_{2nn}—O—)_{mm}C_{nn}H_{2nn}—B_1—CO—CH(R^{21})—(CH_2)_{kk}— \qquad (XXIII),$$

a polyoxyalkylene bridge member of the formula XXIV $$—COCH(R^{21})CH_2NH(C_{nn}H_{2nn}O)_{mm}C_{nn}H_{2nn}—NHCH_2—CH(R^{21})CO— \qquad (XXIV)$$

a polyoxyalkylene bridge member of the formula XXV $$—YY—O—CO—(CH_2)_2—NH—(C_{nn}H_{2nn}—O—)—C_{nn}H_{2nn}—NH—(CH_2)_2COO—YY— \qquad (XXV),$$

a polyoxyalkylene bridge member of the formula XXVI $$—(C_{nn}H_{2nn}—O—)_{mm}C_{nn}H_{2nn}— \qquad (XXVI),$$

and a polyoxyalkylene bridge member of the formula XXVII $$—CH(CH_3)—CH_2—(O—CH(CH_3)—CH_2)_a—(O—CH_2—CH_2)_b—(O—CH_2—CH(CH_3)_c— \qquad (XXVII),$$

wherein a+c=2.5 and b=8.5 to 40.5 or a+c=2 to 33 and b=0,
$R^{21}$ is hydrogen or $C_1$–$C_{16}$ alkyl,
$R^{22}$ is halogen or —O—$R^{23}$,
$R^{23}$ is hydrogen, $C_1$–$C_6$ alkyl, $C_3$–$C_6$ alkenyl, aryl, or aryl-$C_1$–$C_4$-alkyl,
$R^{24}$ is hydrogen, $C_1$–$C_{12}$ alkyl or aryl,
$R^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl,
$R^{26}$ is hydrogen or $C_1$–$C_4$ alkyl,
$R^{27}$ is hydrogen, $C_1$–$C_{18}$ alkyl, $C_3$–$C_6$ alkenyl, $C_1$–$C_{18}$ alkoxy, halogen or aryl-$C_1$–$C_4$ alkyl,
$R^{28}$ and $R^{29}$ independently of one another are hydrogen, $C_1$–$C_{18}$ alkyl, $C_3$–$C_6$ alkenyl, or $C_1$–$C_{18}$ alkoxy, or halogen;
$R^{30}$ is hydrogen, $C_1$–$C_4$ alkyl or CN,
YY is unsubstituted or substituted $C_2$–$C_{20}$ alkyl,
$B_1$ is NH or O;
kk is zero or an integer from 1–16,
mm is an integer from 2 to 60,
nn is an integer from 2 to 6,
u is an integer from 1 to 4;
when r is 3, D is $$—[(CH_2)_s—COO]_3—R^{19}$$

and when r is 4, D is

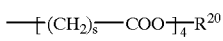

wherein $R^{19}$ is $C_3$–$C_{10}$ alkanetriyl and $R^{20}$ is $C_4$–$C_{10}$ alkanetetryl; and s is 1–6;

$R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —SO$_2$—, —CH$_2$—, or —C(CH$_3$)$_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms; and

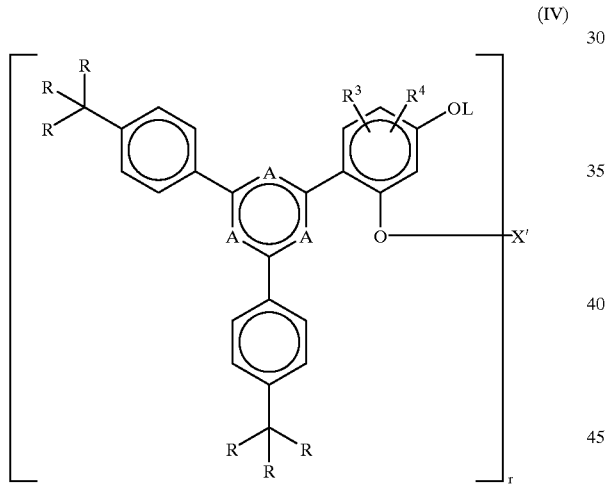

(IV)

wherein

A, R, $R^3$, $R^4$, and L, are as defined above; r is 2 or 3;

X', when r is 2, is —CO—$R^{16}$—CO—, —CO$_2$—$R^{16}$—CO$_2$—,

—SO$_2$—$R^{16}$—SO$_2$—, —CO—NH—$R^{17}$—NH—CO—, a polyoxyalkylene bridge member of formula —CO—(CH$_2$)$_u$—O—(CH$_2$—(CH$_2$)$_u$—O—)$_{mm}$—(CH$_2$)$_u$—CO—, or —COCH($R^{21}$)CH$_2$NH($C_{nn}H_{2nn}$O)$_{mm}C_{nn}H_{2nn}$—NHCH$_2$—CH($R^{21}$)CO— wherein $R^{16}$ and $R^{17}$ are as defined above.

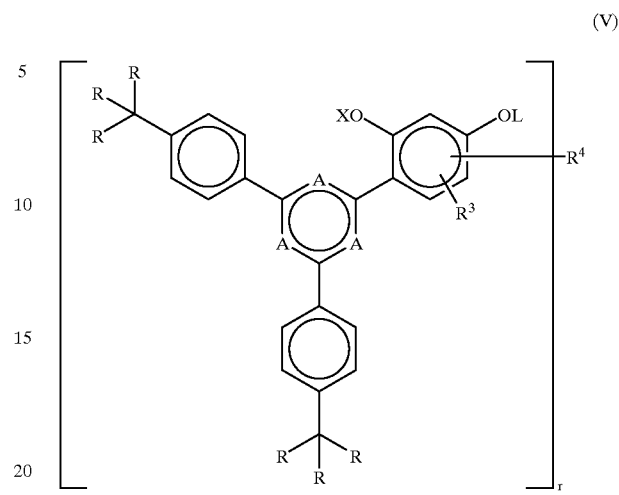

(V)

wherein A, $R^3$, L and X, are as defined above;

$R^4$ is selected from the group consisting of straight chain alkyl of 1 to 12 carbon atoms, branched chain alkyl of 1 to 12 carbon atoms, cycloalkyl of 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —SO$_2$—, —SO—E—SO—, —SO$_2$—E—SO$_2$—, —CH$_2$—NH—E—NH—CH$_2$—, and

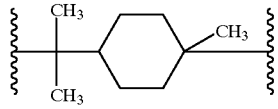

wherein E is selected from the group consisting of alkyl of 2 to 12 carbon atoms, cycloalkyl of 5 to 12 carbon atoms, alkyl interrupted by cyclohexyl of 8 to 12 carbon atoms, alkyl terminated by cyclohexyl of 8 to 12 carbon atoms; and r is an integer between 2 and 4.

The para-tertiary alkyl phenyl substituted pyrimidines and triazines of the present invention further comprise a compound of formula (XXXIV):

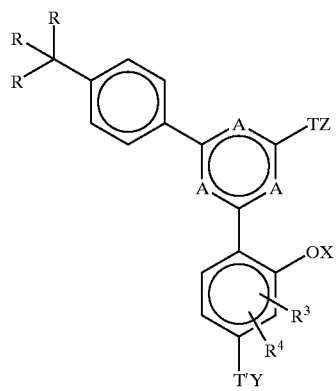

(XXXIV)

wherein
A, X, R, $R^3$, and $R^4$ are defined as in claim 1;
each of T and T' is independently a direct bond, carbon, oxygen, nitrogen, sulfur, phosphorous, boron, silicon, or functional groups containing these elements;
each of Y and Z are each of Y, Z, $R^3$ and $R^4$ are independently a hydrogen, hydrocarbyl group, a functional hydrocarbyl group, halogen, hydroxyl, cyano, —O(hydrocarbyl), —O(functional hydrocarbyl), —N(hydrocarbyl)(hydrocarbyl), —N(functional hydrocarbyl)(functional hydrocarbyl), —N(hydrocarbyl)(functional hydrocarbyl), —S(hydrocarbyl), —S(functional hydrocarbyl), —SO$_2$(hydrocarbyl), —SO$_2$(hydrocarbyl), —SO$_3$(hydrocarbyl), —SO$_3$(functional hydrocarbyl), —COO(hydrocarbyl), —COO(functional hydrocarbyl), —CO(hydrocarbyl), —CO(functional hydrocarbyl, —OCO(hydrocarbyl), —OCO(functional hydrocarbyl), —N(hydrocarbyl)(hydrocarbyl), —CONH$_2$, —CONH(hydrocarbyl), —CONH(functional hyrdocarbyl), —CON(hydrocarbyl)(hyrdocarbyl), —CON(hydrocarbyl)(functional hyrdocarbyl), —CON(functional hydrocarbyl)(functional hyrdocarbyl), —S(functional hydrocarbyl), —SO$_2$(functional hydrocarbyl), —SO$_3$(functional hydrocarbyl), —COO(functional hydrocarbyl), —CO(functional hydrocarbyl), —OCO(functional hydrocarbyl), or a hydrocarbyl group substituted by any of the above groups.

The substituted pyrimidines and triazines of the present invention may optionally have the added benefit of being capable of being chemically bonded to appropriate polymer systems via functionality attached to the alkylphenyl, pyrimidine and triazine groups (e.g., by a hydroxyl, ethylenic unsaturated and/or activated unsaturated group in one or more of $R^1$, $R^2$, Y or Z)

These para-tertiary alkyl phenyl substituted pyrimidines and triazines may in general be prepared via a number of procedures well known in the art, for example, those described in Brunetti, H; Luethi, C.; *Helv. Chemica Acta*, 55 (1972) pp. 1566–1595; Tanimoto, S.; Yamagata, M. Senryo to Yakahin, 40 (1995) pp 339ff; EP 779,280A1; Japanese Patent Kokai Tokkyo Koho 9,059,263; and by Friedel-Crafts reaction starting with a chloro-substituted triazine or pyrimidine.

The novel para-tertiary alkyl phenyl substituted pyrimidines and triazines of the present invention are particularly useful as ultraviolet light absorber agents for stabilizing a wide variety of materials including, for example, organic compounds, oils, fats, waxes, cosmetics, dyes and biocides, and particularly various organic polymers (both crosslinked and non-crosslinked) used in applications such as photographic materials, plastics, fibers or dyed fibers, rubbers, paints and other coatings, and adhesives. The present invention, consequently, also relates to (1) a method of stabilizing a material which is subject to degradation by actinic radiation (e.g., an organic material such as an organic polymer in the form of a film, fiber, shaped article or coating) by incorporating into said material an amount of an actinic radiation stabilizer composition effective to stabilize the material against the effects of actinic radiation, wherein the actinic radiation stabilizer composition comprises the inventive para-tertiary alkyl phenyl substituted 1,3,5-triazine or pyrimidine; and (2) the material so stabilized.

The novel para-tertiary alkyl phenyl substituted pyrimidines and triazines of the present invention are also effective as ultraviolet light screening agents in applications such as sunscreens and other cosmetic preparations, capstock layers for extruded polymers, dyed fibers and laminated UV-screening window films, among others. The present invention, consequently, also relates (1) to a method of protecting a substrate against degradation by actinic radiation by applying to the substrate an actinic radiation screening layer (e.g., a coating film or capstock layer) containing an actinic radiation screening composition in an amount effective to reduce the amount of actinic radiation impinging on the substrate, wherein the actinic radiation screening composition comprises the inventive para-tertiary alkyl phenyl substituted pyrimidines and triazines; and (2) the substrate so protected.

The novel para-tertiary alkyl phenyl substituted pyrimidines and triazines of the present invention may also be employed to form light stabilizing compositions. Such light stabilizing compositions may include a variety of other components known in the art including other ultraviolet light absorbers of the triazine class, other ultraviolet light absorbers of different classes (e.g. benzotriazoles, benzophenones), hindered amine light stabilizers, radical scavengers, antioxidants and the like.

These and other features and advantages of the present invention will be more readily understood by those of ordinary skill in the art from a reading of the following detailed description.

DETAILED DESCRIPTION OF THE PREFERRED EMBODIMENTS

The Para-tertiary Alkyl Phenyl Substituted Pyrimidines and Triazines

As used herein, the term "para-tertiary alkyl phenyl substituted pyrimidines and triazines" broadly refers to any compound of formulas (I) through (V), above.

As used herein, the term "para-tertiary alkyl phenyl" broadly refers to any compound or substituent of general formula:

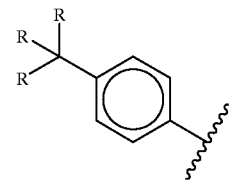

wherein substituent R is as above for general formulas (I)–(V).

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal reactive and/or latent reactive functionality and/or leaving groups. "Reactive" functionality refers to functionality which is reactive with common monomer/polymer functionality under normal conditions well understood by those persons of ordinary skill in the relevant art. As non-limiting examples of reactive functionality may be mentioned active hydrogen containing groups such as hydroxyl, amino, carboxyl, thio, amido, carbamoyl and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene). "Latent reactive" functionality within the meaning of the present invention and, as would clearly be understood by those persons of ordinary skill in the art, refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention, as would clearly be understood by those persons of ordinary skill in the relevant art, is a substituent attached to the hydrocarbyl chain or ring which during reaction is dislodged or displaced to create a valency on a carbon or hetero atom in the hydrocarbyl chain or ring, said valency being filled by a nucleophile. As examples of leaving groups may be mentioned halogen atoms such as chlorine, bromine and iodine; hydroxyl groups (protonated and unprotonated); quaternary ammonium salts ($NT_4^+$); sulfonium salts ($ST_3^+$); and sulfonates ($—OSO_3T$); where T is, e.g., methyl or para-tolyl. Of all these classes of reactive functionality, the preferred functionality includes hydroxyl, $—COOR^5$, $—CR^6=CH_2$, $—CO—CR^6=CH_2$, Cl, an isocyanate group, a blocked isocyanate group and $—NHR^5$, wherein $R^5$ is selected from hydrogen and a hydrocarbyl (preferably of up to 24 carbon atoms); and $R^6$ is selected from hydrogen and an alkyl of 1 to 4 carbon atoms (preferably hydrogen and methyl).

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, alkylaryl, etc.).

The term "functional hydrocarbylene" in the context of the present invention refers to a species of hydrocarbylene possessing pendant reactive functionality, latent reactive functionality and/or leaving groups. The term "non-functional hydrocarbylene" in the context of the present invention refers generally to a hydrocarbylene other than a functional hydrocarbylene.

The para-tertiary alkyl phenyl substituted pyrimidines and triazines in accordance with the present invention also relate to latent stabilizing compounds against actinic radiation of the general formulas (I)–(V), wherein at least one of the hydroxyl groups on the aryl ring ortho to the point of attachment to the triazine or pyrimidine ring is blocked, that is, wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high cleavage rate of the O—X bond and a long shelf life. The use of latent stabilizing compounds is further described in U.S. Pat. Nos. 4,775,707, 5,030,731, 5,563,224 and 5,597,854, which are incorporated herein for all purposes as if fully set forth.

Latent stabilizing compounds comprising the para-tertiary alkyl phenyl substituted pyrimidines and triazines in accordance with the present invention can be prepared from compounds of the general formulas (I)–(V), wherein at least one X is hydrogen, by subjecting said compounds to a further reaction to form latent stabilizing compounds, as described in the immediately preceding incorporated references.

As preferred examples of blocking groups X may be mentioned one or more of the following groups: allyl, $—COR^a$, $—SO_2R^b$, $SiR^cR^dR^e$, $—PR^fR^g$ or $—POR^fR^g$, $—CONHR^h$, wherein each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, $—CH_2—CO—CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, $—CH_2—CO—CH_3$, and phenyl which is unsubstituted or substituted by $C_1$–$C_{12}$ alkyl, $C_2$–$C_8$ alkenyl, $C_1$–$C_4$ alkoxy, halogen and/or benzyl.

The reaction to give the latent stabilizing compounds of the present invention of the general formula (I) and (II), in which X is allyl, $—COR^a$, $—SO_2R^b$, $—SiR^cR^dR^e$, $—PR^fR^g$ or $—POR^fR^g$, can be carried out, for example, by reaction of the compounds of the general formula (III) through (V), wherein at least one X is hydrogen with the corresponding halides such as allyl chloride, $Cl—COR^a$, $Cl—SO_2R^b$, $Cl—SiR^cR^dR^e$, $Cl—PR^fR^g$, or $Cl—POR^fR^g$. The reaction to give the latent stabilizing compounds of the present invention of the general formulas (III) through (V) in which X is $—CONHR^h$ can be carried out, for example, by reaction of the compounds of the general formulas (III) through (V), wherein at least one X is hydrogen with the corresponding isocyanates. Furthermore, acylated compounds can be obtained by reaction with anhydrides, ketenes or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound of the general formula (I) or (II).

Catalysts customarily used for acylation, sulfonylation, phosphonylation, silylation or urethanation reactions may be used in forming the latent stabilizing substituted pyrimidines and triazines of the present invention. For example, acylation and sulfonylation reaction catalysts such as tertiary or quaternary amines, such as triethylamine, dimethylaminopyridine or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, or without a solvent. Alternatively, the reagent(s) may be employed as the solvent. The reaction temperature is usually between room temperature and about 150° C., for example, up to the boiling point of the solvent when a solvent is used.

In preferred embodiments, each X is hydrogen.

In preferred embodiments, L is selected from the group consisting of hydrogen, $C_1$–$C_{24}$ alkyl or mixtures thereof; $C_1$–$C_{24}$ branched alkyl or mixtures thereof; $C_3$–$C_6$ alkenyl; —$COR^{12}$; —$COOR^{12}$; —$CONHR^{12}$; —$SO_2R^{13}$; $C_1$–$C_{18}$ alkyl which is substituted with one or more of the groups:

hydroxy, $C_1$–$C_{18}$ alkoxy, $C_3$–$C_{18}$ alkenoxy, halogen, phenoxy, $C_1$–$C_{18}$ alkyl-substituted phenoxy, $C_1$–$C_{18}$ alkoxy-substituted phenoxy, halogen-substituted phenoxy, —COOH, —$COOR^9$, $CONH_2$, —$CONHR^9$, —$CON(R^9)(R^{10})$, —$NH_2$, —$NHR^9$, —$N(R^9)(R^{10})$, —$NHCOR^{11}$, $N(R^9)COR^{11}$, —$NHCOOR^{11}$, —$N(R^9)$ $COOR^{11}$, —CN, —$OCOR^{11}$, —$OC(O)NHR^9$, —OC $(O)N(R^9)(R^{10})$, $C_2$–$C_{50}$ alkyl which is interrupted by one or more oxygen atoms or carbonyl groups and optionally substituted by one or more substituents selected from the group consisting of hydroxy, $C_1$–$C_{12}$ alkoxy, and glycidyloxy; glycidyl; and cyclohexyl optionally substituted with hydroxyl or —$OCOR^{11}$.

$R^9$ and $R^{10}$ independently of one another are $C_1$–$C_{12}$ alkyl, $C_3$–$C_{12}$ alkoxyalkyl, $C_4$–$C_{16}$ dialkylaminoalkyl, or $C_5$–$C_{12}$ cycloalkyl, or $R^9$ and $R^{10}$ taken together are $C_3$–$C_9$ alkylene or $C_3$–$C_9$ oxoalkylene or $C_3$–$C_9$ azaalkylene.

$R^{11}$ is $C_1$–$C_{18}$ alkyl, $C_2$–$C_{18}$ alkenyl, or phenyl.

$R^{12}$ is $C_1$–$C_{18}$ alkyl, $C_2$–$C_{18}$ alkenyl, phenyl, $C_1$–$C_{12}$ alkoxy, phenoxy, $C_1$–$C_{12}$ alkylamino; phenylamino, tolylamino or naphthylamino and $R^{13}$ is $C_1$–$C_{12}$ alkyl, phenyl, naphthyl or $C_7$–$C_{14}$ alkylphenyl.

Some of these groups as well as others are decribed in U.S. Pat. No. 5,106,891, U.S. Pat. No. 5,189,084, U.S. Pat. No. 5,356,995, U.S. Pat. No. 5,637,706, U.S. Pat. No. 5,726,309, EP 434,608, EP 704,437, WO 96/28431, and GB 2,293,823 which are incorporated herein by reference for all purposes as if fully set forth.

L may also be an alkyl of 1–24 carbon atoms substituted by a hindered amine light stabilizer (HALS) of the general formula (VI). Triazines containing tetramethylpiperidine groups are described in U.S. Pat. No. 4,161,592 and U.S. Pat. No. 5,376,710 which are incorporated herein by reference for all purposes as if fully set forth.

(VI)

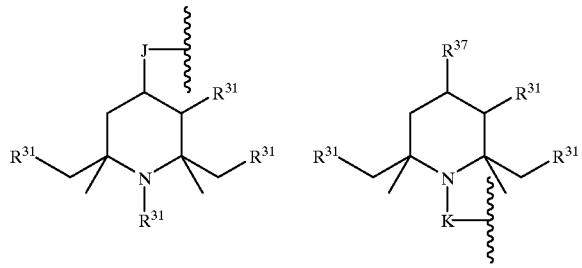

wherein

J is —O—, —$NR^{30}$—, —T—$(CH_2)2$—$NR^{30}$— wherein T is —O— or —S—, and $R^{30}$ is $C_1$–$C_{12}$ alkyl or hydrogen;

$R^{31}$ is hydrogen or $C_1$–$C_8$ alkyl;

$R^{32}$ is hydrogen, oxygen, $C_1$–$C_{21}$ alkoxyalkyl, $C_7$–$C_8$ aralkyl, 2,3-epoxypropyl, and aliphatic acyl group with 1–4 C atoms or one of the groups —$CH_2COOR^{33}$, —$CH_2$—$CH(R^{34})$—$OR^{35}$, —$COOR^{36}$ or —$CONHR^{36}$, wherein $R^{33}$ is $C_1$–$C_{12}$ alkyl, $C_3$–$C_6$ alkenyl, phenyl, $C_7$–$C_8$ aralkyl or cyclohexyl, $R^{34}$ is a hydrogen, methyl or phenyl, $R^{35}$ is hydrogen, an aliphatic, aromatic, araliphatic or alicyclic acyl group with 1–8 C atoms, wherein the aromatic part is unsubstituted or is substituted by chlorine, $C_1C_4$ alkyl, $C_1$–$C_8$ alkoxy or by hydroxyl, and $R^{36}$ is $C_1$–$C_{12}$ alkyl, cyclohexyl, phenyl or benzyl;

$R^{37}$ is hydrogen, —OH or one of the groups —O—CO—$R^{38}$ or —$NR^{36}$—CO—$R^{38}$, wherein $R^{38}$ is $C_1$–$C_{12}$ alkyl or phenyl; and K is —O—$(C_{mm}H_{2mm})$— wherein mm is 1 to 6.

Most preferably, each L group is independently selected from hydrogen, an alkyl of 1 to 24 carbon atoms, or mixtures thereof; an alkyl of 4 to 20 carbon atoms containing one or more oxygen atoms in the chain and optionally substituted with one or more hydroxyl groups, or mixtures thereof.

In preferred embodiments, each $R^3$ and $R^4$ is independently selected from hydrogen, halogen, a hydrocarbyl group of 1 to 24 carbon atoms, a hydrocarbyloxy group of 1 to 24 carbon atoms, an acyl group of 2 to 24 carbon atoms, an acyloxy group of 2 to 24 carbon atoms and —OR. More preferably, each $R^3$ and $R^4$ is independently selected from hydrogen, an alkyl of 1 to 24 carbon atoms optionally containing an oxygen atom in the chain; an alkyloxy of 1 to 24 carbon atoms i an alkenyl of 2 to 24 carbon atoms (which may optionally be substituted by hydroxyl, carboxyl and/or amino group(s) and/or contain carbonyl, oxygen and/or nitrogen in the chain); an alkenyloxy of 2 to 24 carbon atoms (which may optionally be substituted by hydroxyl, carboxyl and/or amino group(s) and/or contain carbonyl, oxygen and/or nitrogen in the chain); a cycloalkyl of 5 to 12 carbon atoms (which may optionally be substituted by hydroxyl, carboxyl and/or amino group(s) and/or contain carbonyl, oxygen and/or nitrogen in the ring); an acyl group of 2 to 12 carbon atoms; optionally substituted benzoyl and —OR. Still more preferably, each $R^3$ and $R^4$ is independently selected from hydrogen, an alkyl of 1 to 24 carbon atoms optionally containing an oxygen atom in the chain, an alkyloxy of 1 to 8 carbon atoms optionally containing an oxygen atom in the chain, a hydroxyalkyl of 1 to 24 carbon atoms group optionally containing an oxygen atom in the chain, a hydroxyalkyloxy of 1 to 8 carbon atoms group optionally containing an oxygen atom in the chain, an acyl group of 2 to 12 carbon atoms, an acyloxy of 2 to 12 carbon atoms and —OR. Especially preferred is when each $R^3$ and $R^4$ is independently selected from hydrogen, an alkyl of 1 to 4 carbon atoms and —OR, and particularly hydrogen and methyl.

In another preferred embodiment, $R^3$ and $R^4$ are independently methylene or alkylidene substituted by a benzophenone UV absorber or a benzotriazole UV absorber. Related triazine Obenzotriazole and triazine-benzophenone hybrid UV absorbers are disclosed in U.S. Pat. No. 5,585,422 which is incorporated by reference herein for all purposes as if fully set forth. In a related preferred embodiment, $R^3$ and $R^4$ are independently methylene, alkylidene, or benzylidene substituted by a second UV absorber. Rekated triazine dimers (and oligomers) are disclosed in U.S. Pat. No. 5,726,309 and EP 704,437 which are incorporated by reference herein for all purposes as if fully set forth.

In preferred embodiments, each of $R^3$ and $R^4$ is independently selected from hydrogen, halogen, acyl of 2 to 24 carbon atoms, benzoyl and substituted benzoyl, alkyl having from 1 to 24 carbon atoms, alkenyl of 2 to 24 carbon atoms, cycloalkyl of 5 to 24 carbon atoms and aralkyl of 7 to 24 carbon atoms.

Further preferred embodiments may include any combination of the parameters mentioned above.

Methods of Preparation

The novel alkyated para-tertiary alkyl phenyl substituted pyrimidines and triazines of the present invention can be prepared through the Friedel-Crafts reaction of an aromatic moiety (XXX) with a halogen-substituted pyrimidine or triazine compound of Formula (XXXI).

The term "Lewis acid" is intended to include aluminum halides, alkylaluminum halides, boron halides, tin halides, titanium halides, lead halides, zinc halides, iron halides, gallium halides, arsenic halide, copper halides, cadmium halides, mercury halides, antimony halides, and the like. Preferred Lewis acids include aluminum trichloride, aluminum tribromide, trimethylaluminum, boron trifluoride, boron trichloride, zinc dichloride, titanium tetrachloride, tin dichloride, tin tetrachloride, or a mixture thereof.

As used herein, the term "acid" includes any inorganic or organic acid with at least one acidic proton, which may or may not be dissolved in an aqueous or organic solution. The organic acids include any organic compound that contains at least one acidic functional group including $RCO_2H$, $RSO_3H$, $RSO_2H$, $RSH$, $ROH$, $RPO_3H$, $RPO_2H$, wherein R is as defined above. Preferred protic acids include HCl, HBr, HI, $HNO_3$, $HNO_2$, $H_2S$, $H_2SO_4$, $H_3PO_4$, $H_2CO_3$, acetic acid, formic acid, propionic acid, butanoic acid, benzoic acid, phthalic acid, oxalic acid, malonic acid, succinic acid, glutaric acid, adipic acid, methanesulfonic acid, and p-toluenesulfonic acid or mixtures thereof.

As used herein, the term "step-wise" means a reaction sequence wherein a series of reactions are conducted, the first reaction producing compounds of Formula (XXXII) and being carried out to between about 50% to about 100% completion prior to addition of a compound of Formula (XXXIII) to produce compounds of Formula (II). Preferably the reaction is carried out to between about 70% to about 100% completion prior to addition of compound of Formula (XXXIII), and more preferably to between about 75% to about 100% completion.

As used herein, the term "continuous" means a reaction sequence not defined as "step-wise."

The novel alkyated para-tertiary alkyl phenyl substituted pyrimidines and triazines of the present invention can be prepared through the Friedel-Crafts reaction of an aromatic moiety (XXX) with a halogen-substituted pyrimidine or triazine compound of Formula (XXXI). See Scheme 1.

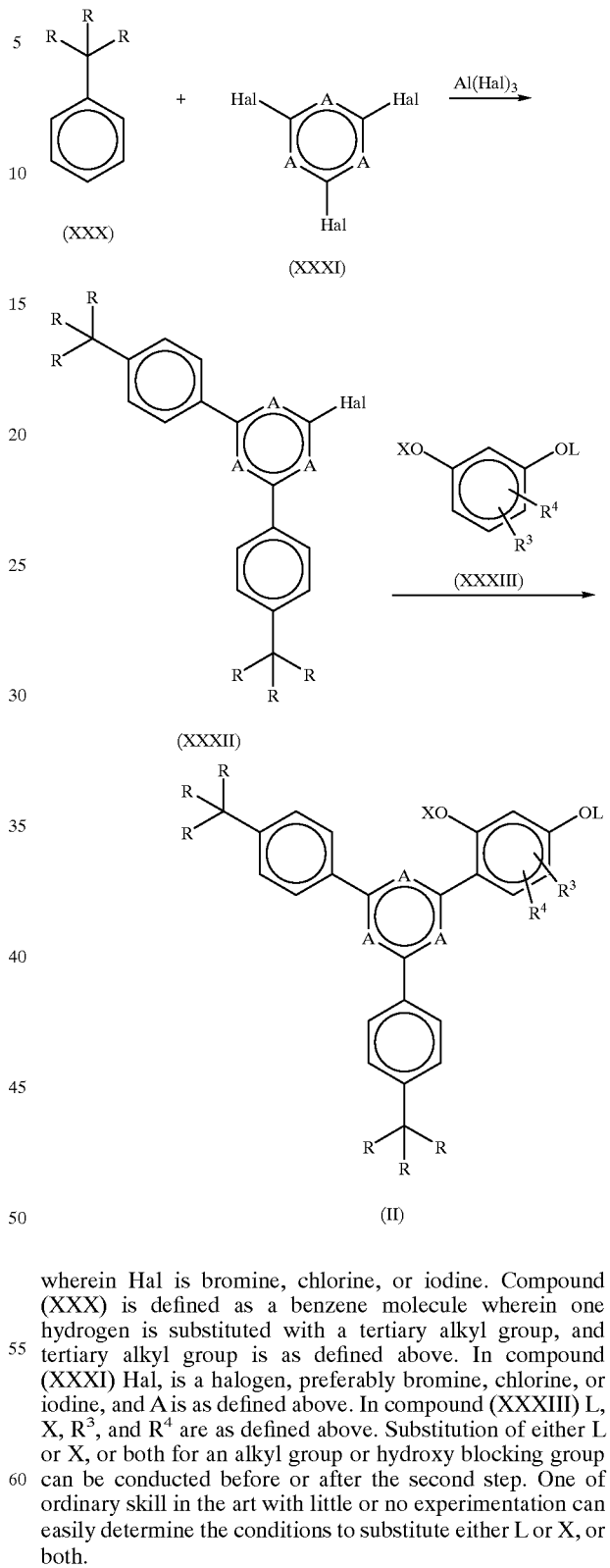

Scheme 1 wherein Hal is bromine, chlorine, or iodine. Compound (XXX) is defined as a benzene molecule wherein one hydrogen is substituted with a tertiary alkyl group, and tertiary alkyl group is as defined above. In compound (XXXI) Hal, is a halogen, preferably bromine, chlorine, or iodine, and A is as defined above. In compound (XXXIII) L, X, $R^3$, and $R^4$ are as defined above. Substitution of either L or X, or both for an alkyl group or hydroxy blocking group can be conducted before or after the second step. One of ordinary skill in the art with little or no experimentation can easily determine the conditions to substitute either L or X, or both.

The relative amounts of the reactants are as follows. The amount of compounds of Formula (XXXI) should be in sufficient amounts to react with aromatic compounds of Formula (XXX) to produce compounds of Formula (XXXII). The amount of aromatic compound of Formula (XXX) is important to ensure that a sufficient amount of aromatic compounds of Formula (XXXII) is synthesized without excessive amounts of undesired side products such as trisaryl triazine or trisaryl pyrimidine. Moreover, excess amounts of aromatic compounds can lead to undesired product distributions enriched in mono- and tris-aryl triazines, or mono- and tris-aryl pyrimidines thus, making product separation and purification difficult and resource consuming.

The amount of aromatic compounds (XXX) should be in sufficient amounts to synthesize 2-halo-4,6-bisaryl-1,3,5-triazine or 2-halo-4,6-bisarylpyrimidine. Preferably, there should be between about 1 to about 5 mol equivalents of aromatic compound of Formula (XXX) to compound of Formula (XXXI). The amount of aromatic compound of Formula (XXXIII) should be between about 0.5 to about 2.5 mol equivalents of aromatic compound of Formula (XXXIII) to compounds of Formula (XXXII).

The amount of Lewis acid, Al(Hal)$_3$ wherein Hal is a halide as defined above, used in the reaction should be in sufficient amounts to transform 2,4,6-trihalo-1,3,5-triazine or 2,4,6-trihalo-pyrimidine to the preferred 2-halo-4,6-bisaryl-1,3,5-triazine or 2-halo-4,6-bisarylpyrimidine, respectively. The amount of Lewis acid should be between about 0.5 to about 500 mol equivalents. Preferably, the amount of Lewis acid should be between about 1 to about 5 mol equivalents.

Advantageously, an acid can be used in conjunction with a Lewis acid when synthesizing compounds of Formula (II) or (XXXII). The amount of acid used in the reaction should be in sufficient amounts to transform 2,4,6-trihalo-1,3,5-triazine or 2,4,6-trihalopyrimidine to the preferred 2-halo-4,6-bisaryl-1,3,5-triazine or 2-halo-4,6-bisarylpyrimidine, respectively, or convert 2-halo-4,6-bisaryl-1,3,5-triazine or 2-halo-4,6-bisarylpyrimidine to the compounds of Formula (II), as desired. Preferably, the amount of acid should be between about 0.01 mol to about 5 mol equivalents.

For synthetic scheme 1, the Lewis acid and acid preferably combine to form a mixture that can be prepared in situ or pre-formed prior to addition to the reagents. The Lewis acid and/or acid can be combined with either aromatic compounds of Formula (XXX), compounds of Formula (XXXI), or both, in any manner. In situ reaction mixture preparation comprises addition of at least one Lewis acid and at least one acid to at least one compound of Formula (XXXI), at least one aromatic compound of Formula (XXX), and optionally solvent, without regard to addition order. To prepare the mixture prior to addition to the reagents, i.e., the pre-formed method, at least one Lewis acid and at least one acid are combined and allowed to mix prior to addition, optionally in an inert solvent. Thereafter, the mixture is added to the reagents or vice versa, as desired and in any addition order. As used herein, one or more Lewis acids may be used, the first step and the second step Lewis acid may be the same or different. Additionally, one or more acids may be used, the first step and second step acid may be the same or different. In the "continuous" process, the use of additional Lewis acid, acid, or both is optional.

If the complex is prepared using the pre-formed method, preferred mixing time of the Lewis acid and acid, prior to addition to the reagents, is between about 1 minute to about 5 hours, more preferred time is between about 10 minutes to about 2 hours. The preferred mixing temperature of the Lewis acid and acid mixture, prior to addition to the reagents, is between about −50° C. to about 100° C., more preferred is between about −10° C. to about −50° C.

The reaction should run for a sufficient amount of time, at a sufficient temperature and pressure to synthesize the desired triazine or pyrimidine compound. The preferred reaction time for the synthesis of compounds of Formula (XXXII), i.e., the first step, is between about 5 minutes and about 48 hours, more preferred between about 15 minutes and about 24 hours. The preferred reaction time for the synthesis of compounds of Formula (II), i.e., the second step, is between about 10 minutes and about 24 hours, more preferably time is between about 30 minutes and about 12 hours. The preferred reaction temperature for the first step is between about −50° C. and about 150° C., more preferred reaction temperature between about −30° C. and about 50° C. The reaction pressure is not critical and can be about 1 atm or higher if desired. Preferably, the reaction is carried out under an inert gas such as nitrogen or argon. The preferred reaction temperature for the second step is between about 0° C. and about 120° C., a more preferred reaction temperature is between about 20° C. and about 100° C.

The step-wise process comprises mixing at least one Lewis acid, at least one acid, and compounds of Formula (XXXI) with one or more of the desired aromatic compounds of Formula (XXX), preferably until the reaction is between about 70% to about 100% completed. Thereafter, the product is isolated and purified. The aromatic compound of Formula (XXXIII) is added to the purified product along with Lewis acid and optionally an acid to synthesize the compounds of Formula (II). The step-wise sequence allows for the isolation, purification, and storage of compounds of Formula (XXXII) prior to subsequent reaction with aromatic compounds of Formula (XXXIII).

The continuous reaction comprises allowing a compound of Formula (XXXI) to react with one or more aromatic compounds of Formula (XXX) in the presence of at least one Lewis acid and at least one acid preferably until the reaction is between about 70% to about 100% complete. Thereafter, without isolating the product of Formula (XXXII), the aromatic compound of Formula (XXXIII) is allowed to react with the product of Formula (XXXII) in the presence of optionally at least one second Lewis acid and optionally at least one second acid preferably until the reaction is between about 70% to about 100% complete. The continuous reaction eliminates the need to purify the intermediate product of Formula (XXXII) or use of additional reagents such as solvents, and optionally Lewis acids and acids. Moreover, the one-step process simplifies the synthetic reaction pathway such that no unnecessary handling or processing of the reaction mixture is required until the reaction is completed.

To synthesize compounds of Formulas (II) or (XXXII) using the pre-formed method, the preferred addition time of the Lewis acid/acid mixture to a reagent mixture is between about 5 minutes to about 5 hours, more preferred time is between about 15 minutes to about 3 hours. The addition temperature of the Lewis acid/acid mixture to a reagent mixture is between about −50° C. to about 150° C., preferred addition temperature is between about −30° C. to about 50° C., and more preferred addition temperature is between about −20° C. to about 80° C.

To synthesize compounds of Formulas (II) or (XXXII) using the pre-formed method, the preferred addition temperature of the Lewis acid/acid mixture is between about 0° C. to about 100° C., preferred addition temperature is between about 20° C. to about 80° C.

To synthesize compounds of Formula (II) the preferred addition time of the aromatic compound of Formula (XXXIII) to the reaction mixture is between about 5 minutes to about 10 hours, more preferred addition time is between about 10 minutes to about 5 hours, and most preferred addition time is between about 15 minutes to about 2 hours. The addition temperature of the aromatic compound of Formula (XXXIII) to the reaction mixture is between about 0° C. to about 150° C., preferred addition temperature is between about 20° C. to about 100° C.

The Lewis acid/acid mixture should be present in amounts sufficient to react with the number of halogens being substituted on compounds of Formula (XXXI). A range of between about 1 to about 5 mol equivalents of Lewis acid and a range of between about 0.01 mol to about 5 mol equivalents of acid can be used. The preferred Lewis acid is aluminum chloride. A preferred amount of Lewis acid is between about 2 to about 4 mol equivalents to halo-triazine or halo-pyrimidine. A preferred amount of acid is between about 0.05 mol to about 2 mol equivalents to compounds of Formula (XXXI).

The synthesis of compounds of Formula (III), (IV), or (V) can be performed by methods commonly known in the art. One of ordinary skill in the art with little or no experimentation can determine the appropriate conditions to obtain the polymer product desired.

Other useful methods of synthesis of substituted triazines are disclosed in the following sources: U.S. Pat. Nos. 5,106,972, 5,438,138, 5,478,935, WO 96/28431, EP 649841, EP 648756, EP 577559, Brunetti, H; Luethi, C.; Helv. Chemica Acta, 55 (1972) pp. 1566–1595; Tanimoto, S.; Yamagata, M. Senryo to Yakahin, 40 (1995) pp 339ff; EP 779,280A1; and Japanese Patent Kokai Tokkyo Koho 9,059,263.

Uses of the Para-tertiary Alkyl Phenyl Substituted Pyrimidines and Triazines

As indicated earlier, the novel para-tertiary alkyl phenyl substituted pyrimidines and triazines of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The novel para-tertiary alkyl phenyl substituted pyrimidines and triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the para-tertiary alkyl phenyl substituted pyrimidines and triazines of the present invention can be employed to stabilize materials which are subject to degradation by ultraviolet radiation by incorporating the presently claimed compounds into polymeric materials, either chemically or physically. Non-limiting examples of polymeric materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfides, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

Further non-limiting examples of specific polymers which may be stabilized include:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).

2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.

3. Hydrocarbon resins (such as $C_5$–$C_9$) including hydrogenated modifications thereof and mixtures of polyalkylenes and starch.

4. Homo- and copolymers of styrenes such as styrene, p-methylstyrene and α-methylstyrene.

5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.

6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.

7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.

8. Homo- and copolymers derived from $\alpha,\beta$-unsaturated acids and derivatives thereof such as acrylic acid, methacrylic acid, acrylates, methacrylates, acrylamides and acrylonitriles.

9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.

10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.

For the preceding groups 1–10 of polymers, the present invention further encompasses these polymers as prepared by metallocene catalysts.

11. Homo- and copolymers of cyclic ethers such as alkylene glycols and alkylene oxides, as well as copolymers with bisglycidyl ethers.

12. Polyacetals such as polyoxymethylene and those polyoxymethylenes which contain ethylene oxide as a comonomer; and polyoxymethylenes modified with thermoplastic polyurethanes, acrylates and/or MBS.

13. Polyphenylene oxides and sulfides.

14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.

15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).

16. Polyureas, polyimides, polyamide-imides, polyetherimides, polyesterimides, polyhydantoins and polybenzimidazoles.

17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; and also polyesters modified with polycarbonate or MBS.

18. Polycarbonates and polyester carbonates.

19. Polysulfones, polyether sulfones and polyether ketones.

20. Crosslinked polymers derived from aldehydes condensation resins such as phenol/formaldehyde resins, urea/formaldehyde resins and melamine/formaldehyde resins.

21. Drying and non-drying alkyd resins.

22. Unsaturated polyester resins derived from copolyesters of saturated and unsaturated dicarboxylic acids with polyhydric alcohols and vinyl compounds as crosslinking agents and also halogen-containing modifications thereof.

23. Crosslinkable acrylic resins derived from substituted acrylates such as epoxy acrylates, hydroxy acrylates, isocyanato acrylates, urethane acrylates or polyester acrylates.

24. Alkyd resins, polyester resins and acrylate resins crosslinked with melamine resins, urea resins, isocyanates, isocyanurates, carbamates or epoxy resins.

25. Crosslinked epoxy resins derived from aliphatic, cycloaliphatic, heterocyclic and/or aromatic glycidyl compounds such as bisphenol A and bisphenol F, which are crosslinked with hardeners such as anhydrides or amines.

26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.

27. Polysiloxanes.

28. Michael addition polymers of amines or blocked amines (e.g., ketimines) with activated unsaturated and/or methylene compounds such as acrylates and methacrylates, maleates and acetoacetates.

29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PATENT/HDPE, PP/HDPE, PP/LDPE, LDPE/HDPE, LDPE/EVA, LDPE/EAA, PATENT/PP, PATENT/PPO, PBT/PC/ABS, PBT/PET/PC and the like.

30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.

31. Radiation curable compositions containing ethylenically unsaturated monomers or oligomers and a polyunsaturated aliphatic oligomer.

32. Epoxymelamine resins such as light-stable epoxy resins cross-linked by an epoxy functional coetherified high solids melamine resin.

Other materials which can be stabilized include, for example:

33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.

34. Aqueous emulsions of natural or synthetic rubber such as natural latex or lattices of carboxylated styrene/butadiene copolymers.

35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.

36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.

37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.

38. Photographic film paper.

39. Ink.

ALIPHATIC POLYAMIDE

The novel alkyated para-tertiary alkyl phenyl substituted pyrimidines and triazines of the present invention can also be used with aliphatic polyamide polymers. An "Aliphatic polyamide" is a polyamide characterized by the presence of recurring carbonamide groups as an integral part of the polymer chain which are separated from one another by at least two aliphatic carbon atoms. Illustrative of these polyamides are those having recurring monomeric units represented by the general formula:

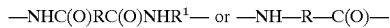

—NHC(O)RC(O)NHR¹— or —NH—R—C(O)— or a combination hereof in which R and R¹ are the same or different and are alkylene groups of at least about two carbon atoms, preferably alkylene having from about 2 to about 12 carbon atoms. Exemplary of such polyamides are polyamides formed by the reaction of diamines and diacids such as poly (tetramethylene adipamide)(nylon 4,6); poly (hexamethylene adipamide) (nylon 6,6); poly (hexamethylene azelamide) (nylon 6,9); poly (hexamethylene sebacamide) (nylon 6,10); poly (heptamethylene pimelamide) (nylon 8,8); poly (nonamethylene azelamide) (nylon 9,9); poly (decamethylene azelamide) (nylon 10,9); and the like. Also illustrative of useful aliphatic polyamides are those formed by polymerization of amino acids and derivatives thereof, as for example lactams. Illustrative of these useful polyamides are poly(4-aminobutyric acid) (nylon 4); poly(6-aminohexanoic acid) (nylon 6); poly(7-aminoheptanoic acid) (nylon 7); poly(8-aminoocatanoic acid) (nylon 8); poly(9aminononanoic acid) (nylon 9); poly(10-aminodecanoic acid) (nylon 10); poly(11-aminoundecanoic acid) (nylon 11); poly(12-aminododecanoic acid) (nylon 12); and the like. Blends of two or more aliphatic polyamides may also be employed.

Copolymers formed from any combination of the recurring units of the above referenced aliphatic polyamides can be used. By way of illustration and not limitation, such aliphatic polyamide copolymers include caprolactam/hexamethylene adipamide copolymer (nylon 6/6,6); hexamethylene adipamide/caprolactam copolymer (nylon 6, 6/6); hexamethylene adipamide/hexamethylene-azelamide copolymer (nylon 6,6/6,9); and copolymers formed from recurring units of the above referenced aliphatic polyamides with aliphatic/aromatic polyamide recurring units may also be used. Examples of such copolyamides are nylon 6/6T; nylon 6,6/6, T; nylon 6/10T; nylon 6/12T; nylon 6,10/6, T etc.

Preferred aliphatic polyamides for use in the practice of this invention are poly(caprolactam); poly(7-aminoheptanic acid); poly(tetramethylene adipamide); poly(hexamethylene adipamide); and mixtures thereof. The particularly preferred aliphatic polyamides are poly(caprolatam); poly (hexamethylene adipamide); poly(tetramethylene adipamide); and mixtures thereof.

Aliphatic polyamides useful in the practice of this invention may be obtained from commercial sources or prepared in accordance with known preparatory techniques. For example, polycaprolactam may be obtained from Allied Signal Inc. and poly(hexamethylene adipamide) may be obtained from DuPont Co.

The number average molecular weight of the aliphatic polyamide may vary widely. Usually, the aliphatic polyamide is of film forming molecular weight that is sufficiently high to form a free standing film and sufficiently low to allow melt processing of the blend into a film. Such number average molecular weights are well known to those of skill in the film art and are usually at least about 5,000 as determined by the formic acid viscosity method. In this method, a solution of 9.2 wt. Concentration of aliphatic polyamide in 90% formic acid at 25° C. is used. In the preferred embodiments of the invention, the number average molecular weight of the aliphatic polyamide is from about 5,000 to about 1,000,000 and in the particularly preferred embodiments is from about 10,000 to about 100,000. Amongst the particularly preferred embodiments, most preferred are those in which the molecular weight of the aliphatic polyamide is from about 20,000 to about 40,000.

POLYURETHANE

Polyurethane (PUR) elastomer products ("spandex") can be stabilized against discoloration and loss of elasticity during UV light exposure with combinations of UV absorbers according to the invention and hindered amine light stabilizers. Spandex fibers is a PUR elastomer product, which requires very specific UV absorber and hindered amine light stabilizers properties in order to achieve optimum performance. UV absorbers of the triazine class of this invention can be combined with polymeric hindered amine light stabilizers (HALS) to provide outstanding performance in achieving the desired properties for the Spandex fiber applications.

The triazine UV absorber of the invention, used alone or in combination with HALS provides the following properties in the Spandex fiber application: (1) low color contribution at typical use levels in the 0.5–2.0% range; (2) sufficient MW, thermal stability and low volatility for fiber processing and thermal exposure conditions; (3) high compatibility and permanence; (4) prevent discoloration and loss of elasticity during exposure to UV light energy; (5) low extraction by water and dry cleaning solvents; (6) low color development during exposure to atmospheric pollutants, $NO_x$, $SO_x$, hydrocarbons, etc.; (7) low interaction with sea water and pool chemicals; (8) low interaction and color development with typical phenolic antioxidants used for the thermal stabilization of Spandex fibers; and (9) low interaction with copper based antioxidant systems used in Nylon fibers for Nylon/Spandex fabrics.

The triazine UV absorber with or without the polymeric HALS provides outstanding stabilization with minimum negative effect on secondary performance properties, such as low color development during $NO_x$ exposure and low interaction with copper based antioxidant systems using in Nylon fibers.

As noted above, any of the triazine compounds disclosed herein can be used to impart one or more of the properties described above to Spandex fibers when added thereto in a stabilization effective amount.

Preferably, these triazine compounds are added in combination with polymeric HALS. The polymeric HALS is preferably poly[(6-morpholino-s-triazine-2,4-diyl)[2,2,6,6,-tetramethyl-4-piperidyl)imino]-hexamethylene [(2,2,6,6-tetramethyl-4-piperidyl)imino]]. Most preferably, the polymeric HALS is the methylated (M) version of the above HALS, which is sold by Cytec Industries, Inc. as CYASORB®UV-3529 light stabilizer. Other polymeric HALS disclosed in U.S. Pat. No. 4,331,586 are also suitable.

Spandex fibers are made from a polyurethane (PUR) prepolymer prepared from a diisocyanate and a glycol. There are four basic processes used to convert the PUR prepolymer into the fiber product. These processes are Solution Dry Spinning, Solution Wet Spinning, Melt Extrusion, and Reaction Spinning. The above UV stabilizer alone or in combination with HALS would be suitable for use in any or all four processes.

Spandex fibers may contain a processing antioxidant system, such as a phenolic antioxidant, or a phenolic/phosphite antioxidant combination. In addition, pigments, such as $TiO_2$ are commonly used in the fiber products.

The triazine UV absorber alone or with M-HALS can be dissolved into DMF or DMAC and added to the PUR prepolymer solution prior to solution fiber spinning processes. Also, the combination can be extrusion compounded into the PUR compound used in the melt spinning process.

POLYCARBONATES

Among polymeric compounds, preference is given to the polycarbonates, polyesters, polyamides, polyacetals, polyphenylene oxides and polyphenylene sulfides, but especially to the polycarbonates. Those compounds are to be understood as being especially those polymers the constitutional repeating unit of which corresponds to the formula:

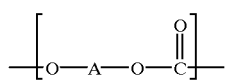

wherein A is a divalent phenolic radical. Examples of A are given inter alia in U.S. Pat. No. 4,960,863 and DE-A-3 922,496. A can be derived, for example, from hydroquinone, resorcinol, dihydroxybiphenylene or bisphenols in the broadest sense of the term, such as bis(hydroxyphenyl) alkanes, cycloalkanes, sulfides, ethers, ketones, sulfones, sulfoxides, α,α'-bis(hydroxyphenyl)-diisopropylbenzenes, for example the compounds 2,2-bis(4-hydroxyphenyl) propane, 2,2-bis(3,5-dimethyl-4-hydroxyphenyl)-propane, 2,2-bis(3,5-dichloro-4-hydroxyphenyl)propane, 1,1-bis(4-hydroxyphenyl)cyclohexane, or from the compounds of the formulae:

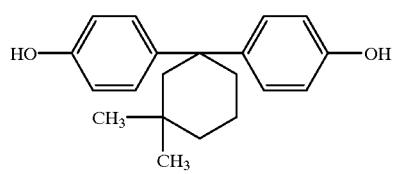

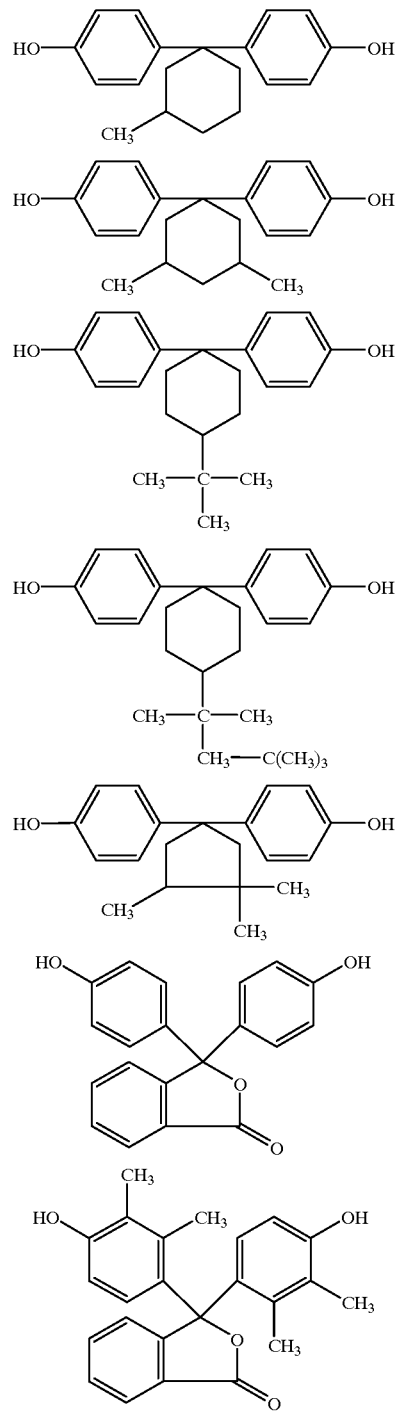

In one embodiment, the preferred resins are polycarbonates based on dihydric phenols such as 2,2-bis-(4-hydroxyphenyl)propane (bisphenol A); 2,4-bis (4-hydroxyphenyl)-2-methylbutane; 1,1-bis-(4-hydroxyphenyl)-cyclohexane; 2,2-bis-(3-chloro-4-hydroxyphenyl)propane; 4,4'-sulfonyldiphenol; and 1,1-bis-(4-hydroxyphenyl)-3,3,5-trimethylcyclohexane.

Also preferred are polycarbonate copolymers incorporating two or more phenols, branched polycarbonates wherein a polyfunctional aromatic compounds is reacted with the dihydric phenol(s) and carbonate precursor, and polymer blends of which polycarbonate comprises a significant portion of the blend.

The most preferred resins for both layers are polycarbonates based on bisphenol A.

U.S. Pat. No. 5,288,788 also describes polycarbonates and polyester carbonates, especially aromatic polycarbonates, for example those based on 2,2-bis(4-hydroxyphenyl) propane or 1,1-bis(4-hydroxyphenyl)cyclohexane.

British Patent Appn. No. 2,290,745 describes a number of methods have been developed to concentrate UV absorbers near or at the surface of polymeric materials. These include surface impregnation (see U.S. Pat. Nos. 3,309,220, 3,043, 709, 4,481,664 and 4,937,026) and coating a plastic article with solutions containing thermoplastic resins and UV absorbers (see U.S. Pat. Nos. 4,668,588 and 4,353,965). Both techniques suffer from drawbacks including requiring additional processing steps (i.e. applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner in known coextrusion equipment as taught in U.S. Pat. Nos. 3,487,505 and 3,557,265. Coextrusion is a well recognized method of producing laminated thermoplastic materials by simultaneously extruding various numbers of layers which form a single composite material. U.S. Pat. No. 4,540,623 describes coextruded materials of at least forty layers. Other methods produce as few as two or three different layers.

In one embodiment, the invention also relates to thermoplastic articles coated with a thermoplastic layer 0.1 to 10 mil (0.00254 mm to 0.254 mm), preferable 0.1 to 5 mil (0.00254 mm to 0.127 mm), thick, in which said layer contains 0.1% to 20% by weight of the para-tertiary alkyl phenyl substituted pyrimidines and triazines of the present nvention. Preferred concentrations of are 2% to 15% by eight; most preferred concentrations of 5% to 10% by weight.

The para-tertiary alkyl phenyl substituted yrimidines and triazines of the present invention may be ncorporated into the thermoplastics of the surfaces layer by standard methods such as dry mixing the additives with granular resin prior to extruding.

The para-tertiary alkyl phenyl substituted pyrimidine or triazine layer may be applied to one or both sides of the thermoplastic article.

Laminated thermoplastic articles which contain additional layers such as a water resistant layer as found in U.S. Pat. No. 4,992,322 are also part of the present invention.

The core layer and the coating layer may be of the same thermoplastic resin or different thermoplastic polyesters, polyester carbonates, polyphenylene oxide, polyvinyl chloride, polypropylene, polypropylene, polyethylene, polyacrylates, polymethacrylates and copolymers and blends such as styrene and acrylonitrile on polybutadiene and styrene with maleic anhydride.

Mixtures (polyblends) of such polymers with one another or with other polymers, for example with polyolefins, polyacrylates, polydienes or other elastomers in the form of impact strength modifiers.

The para-tertiary alkyl phenyl substituted pyrimidines and triazines of the present invention can also be chemically bonded to substrates, such as polymers, thereby greatly reducing the migration of such UV absorbers, e.g., out of the substrate or away from the substrate surface. The bonding mechanism of the triazines of the present invention involves the formation of a bond (chemical and/or co-valent) between a functionality attached to the amido or carbamate group, e.g., by a pendant vinyl or hydroxyl group, and the "host" substrate, such as a polymer.

Incorporation of the para-tertiary alkyl phenyl substituted pyrimidines and triazines of the invention can be brought about by copolymerization, copolyaddition, copolycondensation, by reaction with a polymer which carries suitable functional groups, or by grafting, in a manner as disclosed in U.S. Pat. Nos. 3,423,360 and 5,189, 084 which are incorporated herein by reference as if fully set forth.

Bonding of the para-tertiary alkyl phenyl substituted pyrimidines and triazines of the invention can occur by polymerization or copolymerization. In the case of the novel triazines of the present invention comprising pendant vinyl groups, polymerization or copolymerization with at least one vinyl monomer, e.g., (meth)acrylic acid, esters of (meth) acrylic acid such as methyl acrylate, amides of (meth)acrylic acid, hydroxyethylacrylate, olefins, vinyl chloride, styrene, butadiene, isoprene and acrylonitrile can be carried out to form homopolymers or copolymers in which the vinyl group is incorporated into the backbone of the polymer. Polymerization or copolymerization can be initiated by initiators, such as free radical, anionic and cationic types, or by actinic radiation, such as UV, electron beam, x-rays and gamma irradiation from a $Co^{60}$ source, as is well known to those in the polymerization art. Polymerization or copolymerization can be carried out in solution, in an emulsion, in a dispersion, in the melt, or in the solid state as is well known to those in the polymerization art.

Also, bonding of the presently claimed para-tertiary alkyl phenyl substituted pyrimidines and triazines compounds of the present invention can be brought about by copolyaddition or copolycondensation. Such incorporation can be made by addition during the synthesis of an addition polymer or copolymer or by condensation during the synthesis of a condensation polymer or copolymer by methods known to those skilled in the art. For example, compounds of the formulas (I)–(V) containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

In addition, compounds of the formulas (I)–(V) can be bonded to a monomeric component which is then incorporated into a polymer or copolymer, e.g., by the free radical initiated addition or copolycondensation methods described above. Analogous methods are disclosed in, for example, U.S. Pat. No. 5,459,222 (incorporated by reference herein for all purposes as if fully set forth) for the bonding of benzotriazole and benzophenone stabilizers to diol precursors which are then incorporated by condensation polymerization into polyurethanes and polyesters to impart UV stabilizing properties to said polymers.

Alternately, the para-tertiary alkyl phenyl substituted pyrimidines and triazines of the invention may also be bonded to polymers by reaction with an oligomer and/or polymer which carries suitable functional groups. For example, at least one triazine compound comprising a vinyl pendant group can be added, optionally with at least one other vinyl monomer or compound comprising a vinyl group, to unsaturated polyester resins, unsaturated polybutadiene oligomers or unsaturated rubbers and then cured by actinic radiation or by a free radical catalyst. Or, at least one triazine compound comprising a terminal functional group, such as hydroxyl or amido, may be reacted with a polymer and/or oligomer such as polyesters, polyurethanes and polydiols with reactive end-groups, partially hydrolyzed polyvinylacetate, epoxy resins, polysiloxanes and polymers comprising maleic anhydride, either in the main chain or as a side-chain, by methods analogous to those well known to those of ordinary skill in the art.

Grafting is yet another way of bonding of the presently claimed para-tertiary alkyl phenyl substituted pyrimidines and triazines to polymers and/or oligomers. Grafting may be carried out in solution, in the melt, or in the solid state with the initiators or actinic radiation types discussed above for polymerization when, for example, the novel triazines of the present invention comprising pendant vinyl groups are used. Such para-tertiary alkyl phenyl substituted pyrimidines and triazines may be grafted to saturated polymers, e.g., polyolefins and their copolymers such as polyethylene, polypropylene and poly(ethylene-vinyl acetate), or to polymers comprising unsaturated moieties, e.g., polybutadiene, polyisoprene, ethylene-propylene-(diene monomer) terpolymers and polystyrene and its copolymers.

The para-tertiary alkyl phenyl substituted pyrimidines and triazines of the present invention may be used in widely varying amounts in such applications depending upon such things as the material to be stabilized and the particular application. However, when employed as a stabilizing additive for materials such as organic polymers, the para-tertiary alkyl phenyl substituted pyrimidines and triazines of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the triazines are utilized in the same relative amounts but based on the total weight of the screening agent.

The novel stabilizers of the present invention may also be employed in a non-bondable capacity, for example, in the stabilization of thermoplastic polymers as set forth in the many of the previously incorporated references. Examples of preferred thermoplastic polymers are polyolefins and polymers comprising heteroatoms in the main chain. Preferred polymers are also thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the novel para-tertiary alkyl phenyl substituted triazine or pyrimidine compound and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices.

The novel mixtures can also be added to the polymers to be stabilized in the form of a masterbatch which comprises these compounds, for example, in a concentration of from about 2.5 to about 25%, preferably from about 5 to about 20% by weight of the polymer.

The novel mixtures can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Depending upon their ultimate end use, the para-tertiary alkyl phenyl substituted pyrimidines and triazines of the present invention may be combined with a variety of additives conventionally employed in the UV stabilizing art. Examples of such additives include but are not limited to:

a. Antioxidants
  (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-($\alpha$-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylundec-1-yl) phenol; 2,4-dimethyl-6-(1-methylheptadec-1-yl) phenol; 2,4-dimethyl-6-(1-methyltridec-1-yl)phenol; and mixtures thereof.
  (ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.
  (iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.
  (iv) Tocopherols such as $\alpha$-tocopherol, $\beta$-tocopherol, $\gamma$-tocopherol, $\delta$-tocopherol, and mixtures thereof (vitamin E).
  (v) Hydroxylated thiodiphenyl ethers such as 2,2'-thiobis (6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.
  (vi) Alkylidenebisphenols such as 2,2'-methylenebis(6-tert-butyl-4-methylphenol); 2,2'-methylenebis(6-tert-butyl-4-ethyiphenol); 2,2'-methylenebis[4-methyl-6-($\alpha$-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-($\alpha$-methylbenzyl)-4-nonylphenol]; 2,2'-methylenebis[6-

(α,α-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O-, - and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl) isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of β-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xiv) Esters of β-(5-tert-butyl-4-hydroxy-3-methylphenyl)propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xv) Esters of β-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; allyldiphenylamine; 4-isopropoxydiphenylamine;

-phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl)amine; 2,6-di-tert-butyl-4-dimethylaminomethylphenol; 2,4'-diaminodiphenylmethane; 4,4'-diaminodiphenylmethane; N,N,N',N'-tetramethyl-4,4'-diaminodiphenylmethane; 1,2-bis[(2-methylphenyl)amino]ethane; 1,2-bis(phenylamino)propane; (o-tolyl)biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono- and dialkylated tert-butyldiphenylamines; 2,3-dihydro-3,3-dimethyl-4H-1,4-benzothiazine; phenothiazine; a mixture of mono- and dialkylated tert-butyl/tert-octyl phenothiazines; a mixture of mono- and dialkylated tert-octylphenothiazines; N-allylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-ol.

b. UV-absorbers and light stabilizers (i) 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-( 3',5'-di-tert-amyl-2'-hydroxphenyl)benzotriazole; 2-(3',5'-bis($\alpha,\alpha$-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; and [R—CH$_2$CH—COO(CH$_2$)$_3$]$_2$ B where R=3'-tert-butyl-4'-hydroxy-5'-2H-benzotriazol-2-ylphenyl.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates such as ethyl $\alpha$-cyano-$\beta,\beta$-diphenylacrylate; isooctyl $\alpha$-cyano-$\beta,\beta$-diphenylacrylate; methyl $\alpha$-carbomethoxycinnamate; methyl $\alpha$-cyano-$\beta$-methyl-p-methoxycinnamate; butyl $\alpha$-cyano-$\beta$-methyl-p-methoxycinnamate; methyl $\alpha$-carbomethoxy-p-methoxycinnamate; and N-($\beta$-carbomethoxy-$\beta$-cyanovinyl)-2-methylindoline.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; and nickel complexes of 1-phenyl-4-lauroyl-5-hydroxypyrazole, with or without additional ligands.

(vi) Sterically hindered amines as well as the N derivatives thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl) succinate; bis(1,2,2,6,6-pentamethylpiperidin-4-yl) sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza- 4-oxospiro[4.5]decane and epichlorohydrin. See also generally U.S. Pat. No. 4,619,956, U.S. Pat. No. 5,106,891, GB-A-2269819, EP-A-0309400, EP-A-0309401, EP-A-0309402 and EP-A-0434608.

(vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-( 2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; and 2-(2-hydroxyphenyl)-4-(4-methoxyphenyl)-6-phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl)pentaerythritol diphosphite; bis(2,46-di-tert-butyl-4-methylphenyl) pentaerythritol diphosphite; bisu(isodecyloxy) pentaerythritol diphosphite; bis(2,4-di-tert-butyl-6-methylphenyl)pentaerythritol diphosphite; bis(2,4,6-tris (tert-butyl)phenyl)pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl) methylphosphite; and bis(2,4-di-tert-butyl-6-methylphenyl) ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers (e.g. ionomers).

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, Theological additives, catalysts, levelling assistants, optical brighteners, flameproofing agents, antistatic agents and blowing agents.

(n) Benzofuranones and indolinones such as those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyl] benzofuran-2-one; 3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

The novel para-tertiary alkyl phenyl substituted pyrimidines and triazines of the present invention can also be employed in multilayer systems. In such systems, a polymer composition having from about 0.1 to about 20% by weight and preferably a relatively high content of novel stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by coextrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the para-tertiary alkyl phenyl substituted pyrimidine or triazine compounds of the present invention.

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel mixtures comprising compounds of the formulas (I)–(V) can be used as stabilizers for coatings, for example for paints such as disclosed in numerous references (see, e.g., U.S. Pat. No. 4,619,956, U.S. Pat. No. 4,740,542, U.S. Pat. No. 4,826,978, U.S. Pat. No. 4,962,142, U.S. Pat. No. 5,106,891, U.S. Pat. No. 5,198,498, U.S. Pat. No. 5,298,067, U.S. Pat. No. 5,322,868, U.S. Pat. No. 5,354,794, U.S. Pat. No. 5,369,140, U.S. Pat. No. 5,420,204, U.S. Pat. No. 5,461,151, U.S. Pat. No. 5,476,937, EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the binder of the coating composition of the presently claimed para-tertiary alkyl phenyl substituted pyrimidines and triazines of the present invention.

Multilayer systems are possible here as well (such as electrocoat/basecoat/clearcoat systems), where the concentration of the novel stabilizer in one or more of the layers, and typically the outer layer such as the clearcoat, can be relatively high, for example from about 0.01 to about 20%, preferably about 0.01 to about 10%, and more preferably about 0.02 to about 5% by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

The binder can in principle be any binder which is customary in industry, for example those described in Ullmann's Encyclopedia of Industrial Chemistry, 5th Edition, Vol. A18, pp. 368–426, VCH, Weinheim 1991 which is incorporated herein by reference. In general, it is a film-forming binder based on a thermoplastic or curable resin, predominantly on a curable resin. Examples of thermoplastic binders include acrylics, polyesters, polyurethanes and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991. Preferred binders include those which comprise a functional acrylate resin and a crosslinking agent.

A wide variety of binders may be employed in such coating systems. Examples of suitable coating compositions containing specific binders include but are not limited to:

1. paints based on ambient curable or thermosetting alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;

10. thermoplastic polyacrylate paints based on thermoplastic acrylate resins or externally crosslinking acrylate resins in combination with etherified melamine resins;

11. paint systems based on siloxane-modified or fluorine-modified acrylate resins.

In addition to the binder and novel para-tertiary alkyl phenyl substituted pyrimidines and triazines of the present invention, the coating composition according to the invention preferably further comprise one or more additional ultraviolet light absorbers, including but not limited to those specifically listed above in section b. The additional UV absorbers may be, for example, another tris-aryl-1,3,5-triazine, a 2-hydroxyphenyl-2H-benzotriazole, a 2-hydroxybenzophenone, an ester of an unsubstituted benzoic acid, an acrylate, an oxamide (oxanilide), or any combination of the above. Preferably, the additional UV absorber is a 2-hydroxyphenyl-2H-benzotriazole and the weight ratio of benzotriazole to amido or carbamate triazine is 4:1 to 1:4. More preferably, the weight ratio of benzotriazole to amido or carbamate triazine is 2:1 to 1:2.

To achieve maximum light stability, it is of particular interest to add sterically hindered amines, examples of which are set out in the above-mentioned section b(vi). The invention therefore also relates to a coating composition which, in addition to the binder, the novel para-tertiary alkyl phenyl substituted pyrimidines and triazines and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

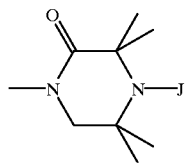

in which J is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

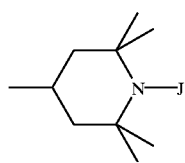

in which J is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. Nos. 4,314,933, 4,344,876, 4,426,471, 4,426,472, 4,619,956, 5,004,770, 5,006,577, 5,064,883, 5,112,890, 5,124,378, 5,106,891, 5,204,473, and 5,461,151, which are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list):

bis(2,2,6,6-tetramethylpiperid-4-yl) succinate, bis(2,2,6,6-tetramethylpiperid-4-yl) sebacate, bis(1,2,2,6,6-pentamethylpiperid-4-yl) sebacate, di(1,2,2,6,6-pentamethylpiperid-4-yl) butyl-(3,5-di-tert-butyl-4-hydroxybenzyl)malonate, bis(1-octyloxy-2,2,6,6-tetramethylpiperid-4-yl) sebacate, tetra(2,2,6,6-tetramethylpiperid-4-yl) butane-1,2,3,4-tetracarboxylate, tetra(1,2,2,6,6-pentamethylpiperid-4-yl) butane-1,2,3,4-tetracarboxylate, 2,2,4,4-tetramethyl-7-oxa-3,20-diaza-21-oxo-dispiro[5.1.11.2]heneicosane, and 8-acetyl-3-dodecyl-1,3,8-triaza-7,7,9,9-tetramethylspiro[4.5]decane-2,4-dione. Commercially available examples of these and other tetraalkylpipieridine derivatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 and 944 (Ciba Specialty Chemicals); and CYASORB® UV-3346, UV 3529, UV-3853, UV-500 and UV-516 (Cytec Industries Inc.).

Apart from the binder, the para-tertiary alkyl phenyl substituted pyrimidine or triazine, and, if used, the additional ultraviolet light absorber or stabilizer, the coating composition can also comprise further components, examples being solvents, pigments, dyes, plasticizers, stabilizers, thixotropic agents, drying catalysts and/or leveling agents. Examples of possible components are those described in many of the previously incorporated references as well as Ullmann's Encyclopedia of Industrial Chemistry, 5th Edition, Vol. A18, pp. 429–471, VCH, Weinheim 1991; and Calbo, Leonard J., ed., Handbook of Coatings Additives, New York:Marcel Dekker (1987).

Possible drying catalysts or curing catalysts are, for example, organometallic compounds, amines, acids, amino-containing resins and/or phosphines.

Examples of acid catalysts are mineral acids, aliphatic and aromatic sulfonic acids (e.g. p-toluene sulfonic acid, dinonylnaphthalene disulfonic acid, dodecylbenzene sulfonic acid), oxalic acid, maleic acid, hexamic acid, phosphoric acid, alkyl phosphate esters, phthalic acid and acrylic acid copolymers.

Examples of organometallic compounds are metal carboxylates, especially those of the metals Pb, Mn, Co, Zn, Zr or Cu, or metal chelates, especially those of the metal Al, It or Zr, or organometallic compounds such as organotin compounds, for example. Examples of metal carboxylates are the stearates of Pb, Mn or Zn, the octoates of Co, Zn or Cu, the naphthenates of Mn and Co or the corresponding linoleates, resinates or tallates. Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate or dibutyltin dioctoate.

Examples of amine drying or curing catalysts are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

Another type of curing catalyst is a peroxide which can be used, for example, to cure a gel coating for a fiberglass article.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The novel coating compositions according to the invention can be applied to any desired substrates, for example to metal, wood, plastic, fiberglass or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. Thermosetting coatings are preferably cured at 50–150° C. and, in the case of powder coatings, even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formulas (I)–(V), according to the invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof; and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition a mixture comprising a compound of a para-tertiary alkyl phenyl substituted pyrimidine or triazine and to the use of mixtures comprising para-tertiary alkyl phenyl substituted pyrimidine or triazine compound in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The para-tertiary alkyl phenyl substituted pyrimidine or triazines of this invention may be applied topically by polishing a surface with a composition comprising the para-tertiary alkyl phenyl substituted pyrimidine or triazines and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics and wood.

Preference is also given to the use of the novel para-tertiary alkyl phenyl substituted pyrimidine or triazine compounds in photographic materials as stabilizer against damage by light, especially by UV light. The invention therefore also relates to a photographic material comprising an para-tertiary alkyl phenyl substituted pyrimidine or triazine compound.

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. Nos. 4,853,471, 4,973, 702, 4,921,966 and 4,973,701), benzophenones, oxanilides, cyanoacrylates, salicylates, or acrylonitriles or thiazolines. In this context it is advantageous to employ these further, oil-dissolved UV absorbers in the photographic material in layers other than those comprising the novel UV absorbers.

The present invention also encompasses compositions containing one or more binders. In particular, the binder may comprise an alkyd, acrylic, polyester, phenolic, melamine, epoxy or polyurethane resin, or blends thereof. Examples of such binders include, but are not limited to:

(a) cold- or hot-crosslinkable alkyd, acrylate, polyester, epoxy or melamine resins or mixtures of such resins;

(b) a two-component polyurethane system comprising hydroxyl-containing acrylate, polyester or polyether resins and aliphatic or aromatic isocyanates, isocyanurates or polyisocyanates;

(c) a one-component polyurethane system comprising blocked isocyanates, isocyanurates or polyisocyanates which are deblocked during baking;

(d) a two-component system comprising (poly)ketimines and aliphatic or aromatic isocyanates, isocyanurates or polyisocyanates;

(e) a two-component system comprising (poly)ketimines and an unsaturated acrylate resin or a polyacetoacetate resin or a methacrylamidoglycolate methyl ester;

(f) a two-component system comprising carboxyl- or amino-containing polyacrylates and polyepoxides;

(g) a two-component system comprising acrylate resins containing anhydride groups and on a polyhydroxy or polyamino component;

(h) a two-component system comprising (poly)oxazolines and acrylate resins containing anhydride groups, or unsaturated acrylate resins, or aliphatic or aromatic isocyanates, isocyanurates or polyisocyanates;

(i) a two-component system comprising unsaturated polyacrylates and polymalonates;

(j) a thermoplastic polyacrylate system comprising thermoplastic acrylate resins or externally crosslinking acrylate resins in combination with etherified melamine resins; and (k) a system comprising siloxane-modified or fluorine-modified acrylate resins.

Such binder-containing compositions may further comprise a curing catalyst, or an organic solvent, and may be radiation-curable. In particular, such compositions may serve as coating compositions.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a para-tertiary alkyl phenyl substituted pyrimidine or triazine compound.

Preference is additionally given to photographic materials which have a layer comprising a compound of the formula (I)–(V) above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the formula (I)–(V) must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride bromide comprising at least 90 mol % of silver chloride.

The compounds of the formula (I)–(V), which are used in accordance with the invention, can be incorporated, alone or together with the color coupler and, if used, further additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids, or alkylamides and phenols.

Preferred color couplers for use in the compositions of the invention, examples of such compounds, further additives such as color cast inhibitors, DIR couplers and further light stabilizers, such as UV absorbers, phenols, phosphorus (III) compounds, organometallic complexes, hydroquinones and hydroquinone ethers, and more precise details on the structure of various photographic materials, can be found, for example, in the publications EP-A-0531258 and EP-A-0520938 and in the literature cited therein.

The invention also relates to a process for the stabilization of polyolefin or polyolefin copolymer films for agricultural applications, especially greenhouse applications, this polyolefin or polyolefin copolymer film having improved light stability and pesticide resistance, comprising incorporation of a sterically hindered amine and a metal oxide of hydroxide selected from oxides of zinc, aluminum, calcium and magnesium, and hydroxides of zinc, aluminum and calcium, into the polyolefin or polyolefin copolymer. A further subject of the invention is a greenhouse, characterized in that it is covered by a polyolefin or polyolefin copolymer film having improved light stability and pesticide resistance and stabilized with a sterically hindered amine and a metal oxide or hydroxide selected from oxides of zinc, aluminum, calcium and magnesium, and hydroxides of zinc, aluminum and calcium, and a process for stabilizing a polyolefin or polyolefin copolymer greenhouse film against detrimental effects of pesticides and light, oxygen and/or heat, which process comprises incorporation of a sterically hindered amine and a metal oxide or hydroxide selected from oxides of zinc, aluminum, calcium and magnesium, and hydroxides of zinc, aluminum and calcium, into said greenhouse film.

Further subjects of the invention are the use of a polyolefin copolymer film stabilized with a sterically hindered amine and a metal oxide or hydroxide selected from oxides of zinc, aluminum, calcium and magnesium, and hydroxides of zinc, aluminum and calcium for agricultural applications involving pesticides, especially greenhouse applications, and the use of a sterically hindered amine in combination with a metal oxide or hydroxide selected from oxides of zinc, aluminum, calcium and magnesium, and hydroxides of zinc, aluminum, calcium and magnesium, and hydroxides of zinc, aluminum and calcium for the stabilization of polyolefin or polyolefin copolymer films in contact with pesticides against photodegradation and damage by pesticides.

To form a film, forcing a quantity of the said melted composition through a film die, such as a flat film die or a circular blown film die, and forming a film therefrom. In the case where the composition is used to form a film therefrom, it is contemplated that the films may be unoriented, or may be subjected to a conventional operation to impart a degree of orientation on the film. Such a film may be oriented in one direction, such as in the machine direction, such as in the "machine direction" and/or the "transverse direction", or may be oriented in both directions, or "biaxially" oriented.

The present invention is also suitable for sheet applications.

The para-tertiary alkyl phenyl substituted pyrimidine or triazine compounds of the formula (I)–(V) are suitable for the photochemical stabilization of undyed, dyed or printed fiber materials comprising for example, silk, leather, wool, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. Preferred textile fiber materials are those of cotton. The triazine and pyrimidine compounds of the present invention are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with a novel compound offer to the human skin.

To this end, one or a number of different compounds of the formula (I)–(V) are applied to the textile fiber material by one of the customary dyeing methods, advantageously in a quantity of 0.01 to 5% by weight, preferably 0.1 to 3% by weight and, in particular, from 0.25 to 2% by weight, based on the weight of the fiber material.

The para-tertiary alkyl phenyl substituted pyrimidine or triazine compounds can be applied to the fiber material in various ways and fixed on the fiber, especially in the form of aqueous dispersions or printing pastes.

The textile fiber materials finished with the novel compounds of the formula (I)–(V) possess improved protection against photochemical breakdown of the fiber and yellowing phenomena and, in the case of dyed fibre material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with an para-tertiary alkyl phenyl substituted pyrimidine or triazine compound has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the formulas (I)–(V) are permeable to UV radiation. The determination of the sun protection factor of textile fiber materials is explained, for example, in WO94/04515 or in J. Soc. Cosmet. Chem. 40, 127–133 (1989) and can be carried out analogously thereto.

Yet another use of the UV absorbers according to the invention is in the stabilization of intra-ocular and contact lenses.

The inventive UV absorbers are suitable as photoprotective agents in cosmetic preparations. The invention additionally relates, therefore, to a cosmetic preparation comprising at least one para-tertiary alkyl phenyl substituted pyrimidine or triazine compound and cosmetically acceptable carriers or auxiliaries.

The novel cosmetic composition contains from 0.1 to 15% by weight, preferably from 0.5 to 10% by weight, based on the overall weight of the composition, of a para-tertiary alkyl phenyl substituted pyrimidine or triazine UV absorber and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase can comprise any oil which is suitable for cosmetic formulations, e.g., one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For these cosmetic formulations, it is possible to use any conventionally employed emulsifier, e.g., one or more ethoxylated esters of naturally occurring derivatives, i.e., polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

The invention will now be illustrated by the following examples. The examples are not intended to be limiting of the scope of the present invention. In conjunction with the general and detailed descriptions above, the examples provide further understanding of the present invention.

EXAMPLES

Examples and reaction schemes for producing specific examples of para tertiary alkyl phenyl substituted triazines in accordance with the invention are provided below. While the following examples illustrate preparations with one or more para tertiary alkylated phenyl compounds, one of ordinary skill will understand that these reactions may also be carried out with any of a variety of other tertiary alkylated phenyl compounds, where when necessary, reactive substituents on such other tertiary alkylated phenyl compounds are protected in accordance with procedures and reagents well known and understood by those of ordinary skill.

PREPARATIVE EXAMPLES

Example 1

Preparation of 2,4-bis(4-tert-butylhenyl)-6-chloro-1,3,5-triazine

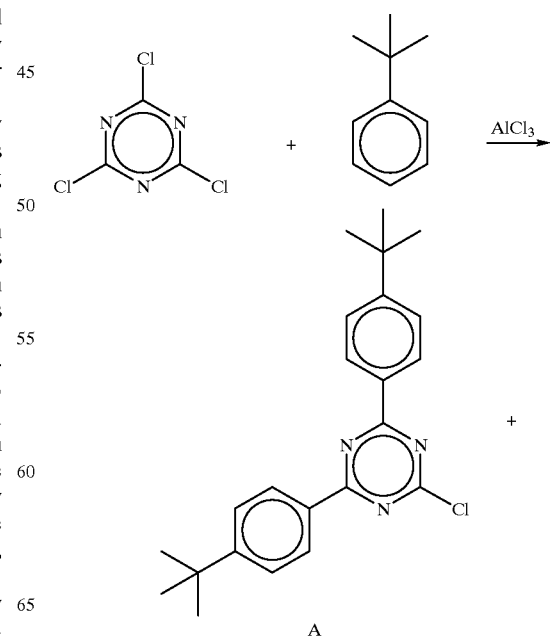

A

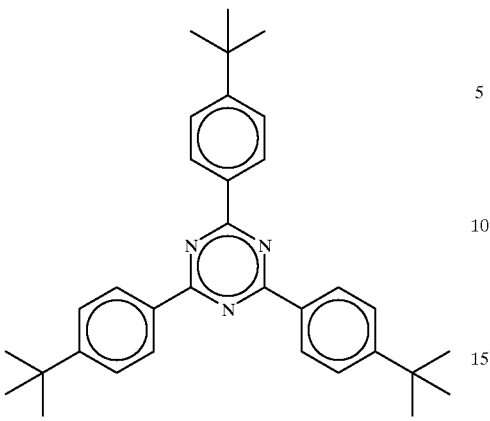

To a 2-neck flask equipped with a reflux condenser, an argon inlet, a magnetic stirring bar and a glass stopper was introduced 9.2 g of cyanuric chloride. To it was added 125 mL of tert-butylbenzene followed by 8 g of aluminum chloride at room temperature. The reaction mixture was then gradually heated to 65° C. and kept at this temperature for 3.5 hr. At this stage an additional 8 g of aluminum trichloride was added and the reaction mixture was heated at 75° C. for 3 hr. The heating was discontinued and the reaction mixture was left at room temperature overnight and then treated with 300 mL of ice-cold dilute HCl for 2 hr. The mixture was extracted with methylene chloride and the organic layer separated, washed with water, dried over anhydrous sodium sulfate and concentrated under reduced pressure to dryness. The residue so obtained was treated with acetone. The precipitated material was filtered off which was characterized to be mainly 2,4,6-tris(4-tert-butylphenyl)-1,3,5-triazine. The filtrate was concentrated and purified by column chromatography to give 4.6 g of a compound characterized to be 2,4-bis(4-tert-butylphenyl)-6-chloro-1,3, 5-triazine.

Example 2

Preparation of 2,4-bis(4-tert-butylphenyl)-6-(2,4-dihydroxyphenyl)-1,3,5-triazine (Compound B)

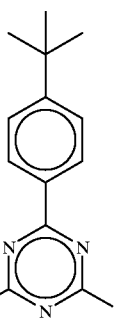

A

+

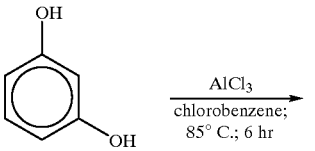

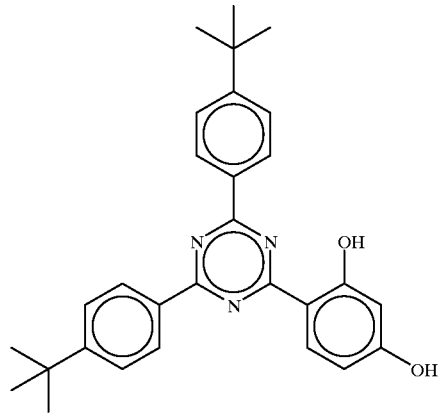

B

To a 2-neck flask equipped with a reflux condenser, an argon inlet, a magnetic stirring bar and a glass stopper was introduced 3.79 g of 2,4-bis(4-tert-butylphenyl)-6-chloro-1, 3,5-triazine of example 1. To it was added 30 mL of chlorobenzene, 1.21 g of resorcinol and 2 g of aluminum chloride at room temperature. The reaction mixture was heated at 85° C. for 6 hr. The heating was discontinued and the reaction was allowed to cool to room temperature. To it was then added 5% ice-cold aq. HCl, and the mixture concentrated under reduced pressure. The residue was washed with water and dried to give 4.4 g of a product characterized to be 2,4-bis(4-tert-butylphenyl)-6-(2,4-dihydroxyphenyl)-1,3,5-triazine.

Example 2
Alternative Procedure

To a stirred suspension of 30 g of cyanuric chloride in 180 mL of o-dichlorobenzene (ODCB) under nitrogen was added 65.1 g of anhydrous aluminum chloride. Concentrated hydrochloric acid (3.9 g) was added over 35 min., maintaining the temperature below 24° C. Thereafter, the mixture was stirred for 2 hr at room temperature. The mixture was cooled to 1° C. and 54.5 g of tert-butylbenzene was added over 2.5 hr, while maintaining the temperature at between about 1° C. to about 4° C. The mixture was then slowly allowed to warm to room temperature and stirred for 20.5 hr. HPLC analysis detected 83% conversion of cyanuric chloride.

The reaction mixture was heated to 65° C. and 18 g of resorcinol was added over 35 min. The mixture was then heated for 2.5 hr at between about 75° C. to about 95° C. The mixture was cooled and 75 mL of methyl isobutyl ketone (MIBK) and 300 mL of 5% aqueous hydrochloric acid were added. The MIBK and ODCB were removed by azeotropic distillation. During this time, the product precipitated. After cooling to room temperature, the aqueous layer was decanted from the solids, the former being triturated with water. The solids were collected by filtration, washed with water, air-dried, and then dried in vacuo.

The dried solid was extracted with methylene chloride and filtered. The filtrate was concentrated under reduced pressure and purified by column chromatography using silica gel and methyl chloride as the eluant. The product crystallized from the eluant to give a yellow solid identified as 2,4-bis(4-tert-butylphenyl)-6-(2,4-dihydroxypheynyl)-1,3,5-triazine by HPLC and HPLC/MS.

Example 3

Preparation of 2,4-bis(4-tert-butylphenyl)-6-(2-hydroxy-4-octyloxyphenyl)-1,3,5-triazine (Compound C)

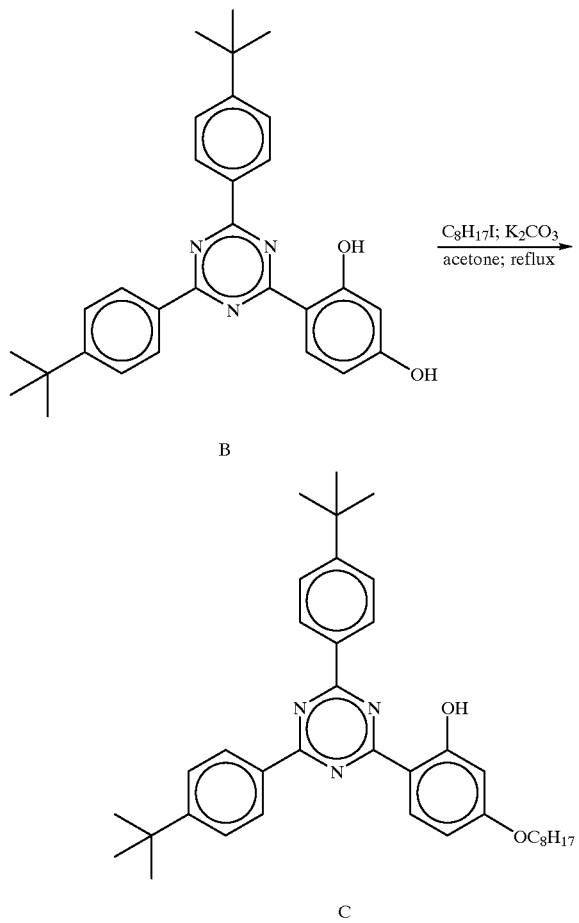

To a 2-neck flask equipped with a reflux condenser, an argon inlet, a magnetic stirring bar and a glass stopper was introduced 2.25 g of 2,4-bis(4-tert-butylphenyl)-6-(2,4-dihydroxyphenyl)-1,3,5-triazine of example 2. To it was added 30 mL of acetone, 3.45 g of anhydrous potassium carbonate and 0.9 mL of 1-iodooctane. The contents were heated to reflux for 6 hr. The reaction mixture was cooled to room temperature, diluted with methylene chloride and filtered through Celite. The filtrate was concentrated under reduced pressure to give 3.7 g of a residue which was purified by column chromatography over silica gel to give 2.26 g of a pure product characterized to be 2,4-bis(4-tert-butylphenyl)-6-(2-hydroxy-4-octyloxyphenyl)-1,3,5-triazine based on NMR and mass spectra.

Example 4

Preparation of 2,4-bis(4-tert-butylphenyl)-6-(2,4-dihvdroxy-5-hexylphenyl)-1,3,5-triazine (Compound D)

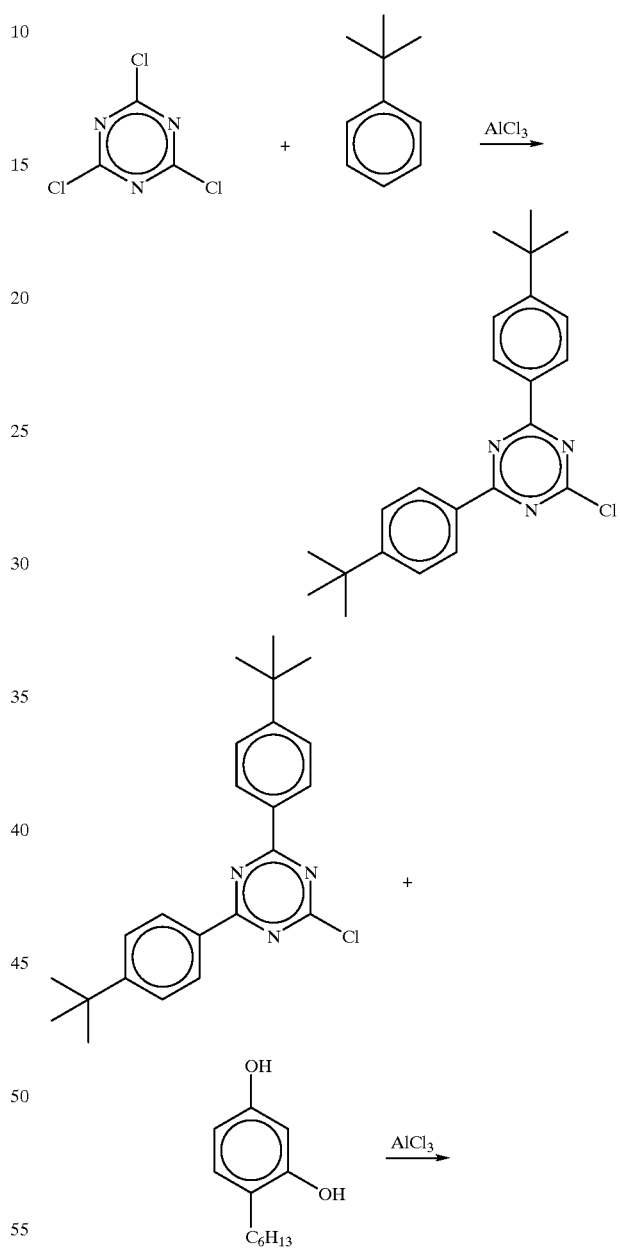

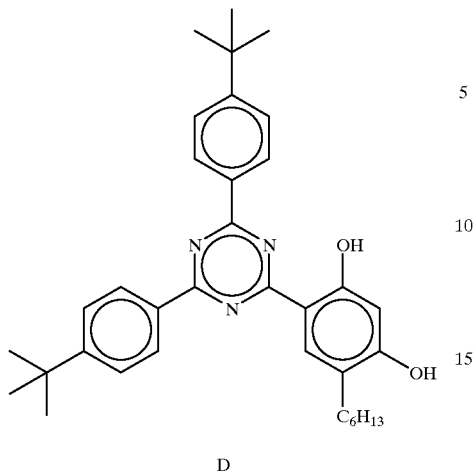

D

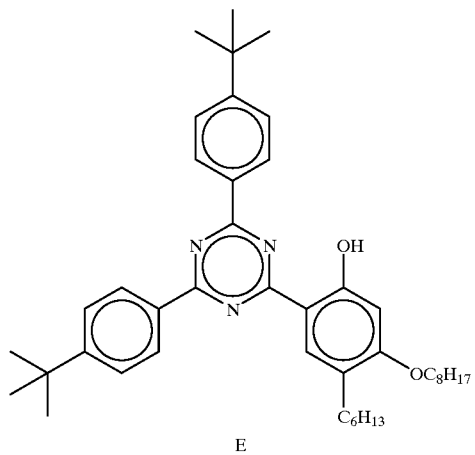

E

To a stirred suspension of 30 g of cyanuric chloride in 180 mL of o-dichlorobenzene (ODCB) under nitrogen was added slowly 65.1 g of aluminum chloride. Concentrated hydrochloric acid (3.9 g) was added over 20 min, maintaining the temperature below 26° C. The reaction mixture was then stirred at room temperature for 2 hr. The mixture was cooled to 0° C. and 54.5 g of tert-butylbenzene was added over 2 hr. The reaction mixture was allowed to warm to room temperature and stirred for 40 hr. HPLC analysis showed complete consumption of cyanuric chloride.

The reaction mixture was heated to 80° C. and 34.7 g of 4-hexylresorcinol was added slowly. After stirring at 80° C. for 3 hr, the reaction mixture was quenched with water and extracted with methylene chloride. The combined methylene chloride extracts were concentrated under reduced pressure. The residue was crystallized from hexane and dried in vacuo to give 31 g of 2,4-bis(4-tert-butylphenyl)-6-(2,4-dihydroxy-5-hexylphenyl)-1,3 5-triazine in >96% purity by HPLC (area % at 290 nm).

Example 5
Preparation of 2,4-bis(4-tert-butylphenyl)-6-(2-hydroxy-4-octyloxy-5-hexylphenyl)-1,3,5-triazine (Compound E)

A stirred mixture of 2,4-bis(4-tert-butylphenyl)-6-(2,4-dihydroxy-5-hexylphenyl)-1,3,5-triazine, 5 g of 1-iodooctane, 1 g of Aliquat® 336 (tricaprylmethylammonium chloride), 14 g anhydrous potassium carbonate, and 200 mL methyl isobutyl ketone (MIBK) was heated at 115–120° C. for 5 hr, and then allowed to cool to room temperature. The mixture was extracted with methylene chloride and the combined methylene chloride extracts were concentrated under reduced pressure. The resulting semi-solid residue was recrystallized from acetone to give 12 g of 2,4-bis(4-tert-butylphenyl)-6-(2-hydroxy-4-octyloxy-5-hexylphenyl)-1,3,5-triazine as a yellow solid in 97% purity as determined by HPLC (area % at 290 nm). A second recrystallization from acetone yielded an analytical sample (100% purity by HPLC).

Example 6

Preparation of 2,4-bis(4-tert-butylphenyl)-6-(2-acetoxy-4-octyloxyphenyl)-1,3,5-triazine (Compound F)

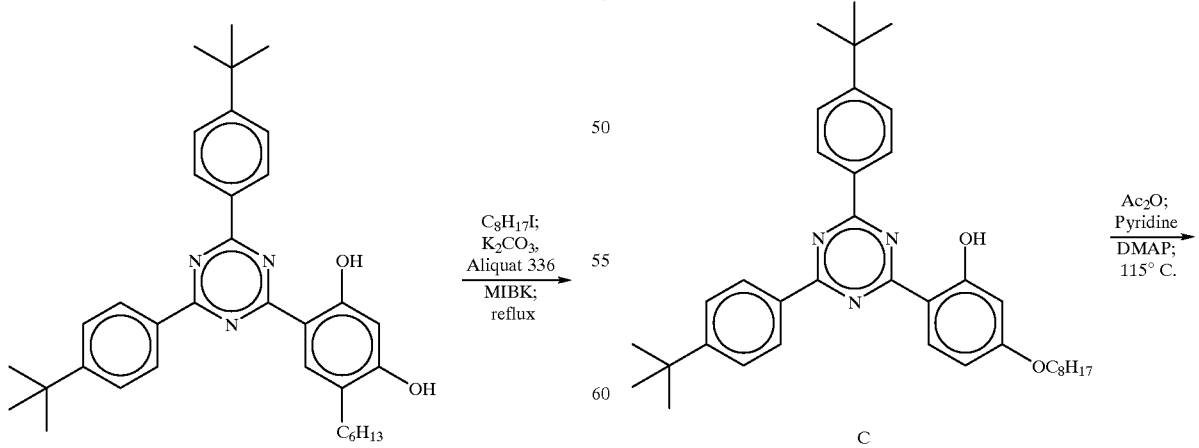

53
-continued

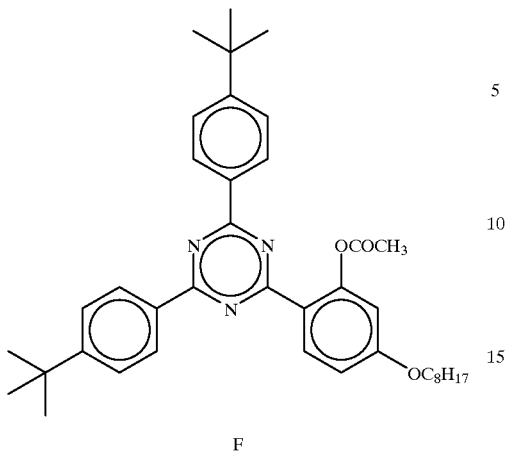

F

54
-continued

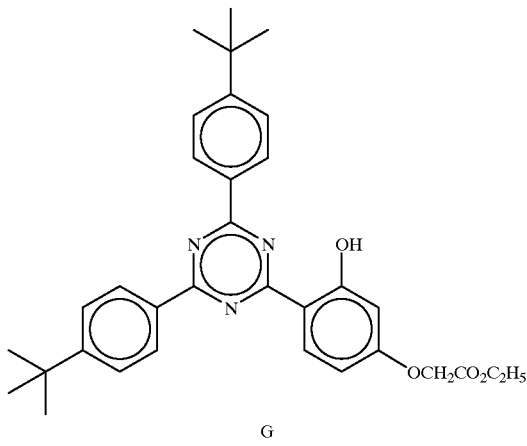

G

To a 2-neck flask equipped with a reflux condenser, an argon inlet, a magnetic stirring bar and a glass stopper was introduced 1.4 g of 2,4-bis(4-tert-butylphenyl)-6-(2-hydroxy-4-octyloxyphenyl)-1,3,5-triazine of example 3. To it was added 5 mL of pyridine, 1.0 mL of pyridine and 25 mg of 4-dimethylaminopyridine. The contents were heated at 115° C. for 3 hr. The reaction mixture was cooled to room temperature and poured into ice-cold water and stirred for 1 hr. The precipitaed material was filtered and dissolved in methylene chloride. The solution thus obtained was first washed with dilute HCl and then with water, dried over anhydrous sodium sulfate and concentrated under reduced pressure. The residue so obtained was crystallized with hexane to give 1.06 g of a pure compound characterized to be 2,4-bis(4-tert-butylphenyl)-6-(2-acetoxy-4-octyloxyphenyl)-1,3,5-triazine based on NMR and mass spectra.

Example 7
Preparation of 2,4-bis-(4-tert-butylphenyl)-6-(2-hydroxy-4-ethoxycarbonylmethoxyphenyl)-1,3,5-triazine (Compound G)

To a stirred mixture of 14 g of 2,4-bis(4-tert-butylphenyl)-6-(2,4-dihydroxyphenyl)-1,3,5-triazine, 10.8 g of anhydrous potassium carbonate, 0.47 g of potassium iodide, and 90 mL of acetone was added 3.7 mL (4,2 g) of ethyl chloroacetate. The mixture was stirred at reflux for 3 hr, and then cooled to room temperature. The solids were removed by filtration and washed with methylene chloride. The product was crystallized from the combined filtrate, washed with cold acetone, and dried in vacuo to give 12.5 g of 2,4-bis(4-tert-butylphenyl)-6-(2-hydroxy-4-ethoxycarbonylmethoxyphenyl)-1,3,5-triazine as a near white powder. The structure was verified by $^1$H-NMR spectroscopy.

Example 8
Preparation of 2-(2-hydroxy-4-ethoxycarbonylmethoxy-5-hexylphenyl)-4,6-bis(4-tert-butylhenyl)-1,3,5-triazine (Compound H)

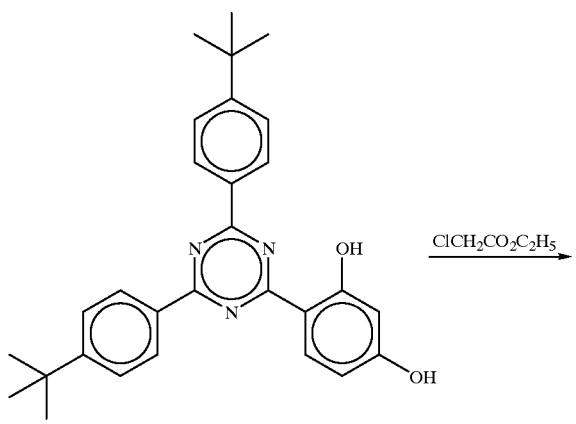

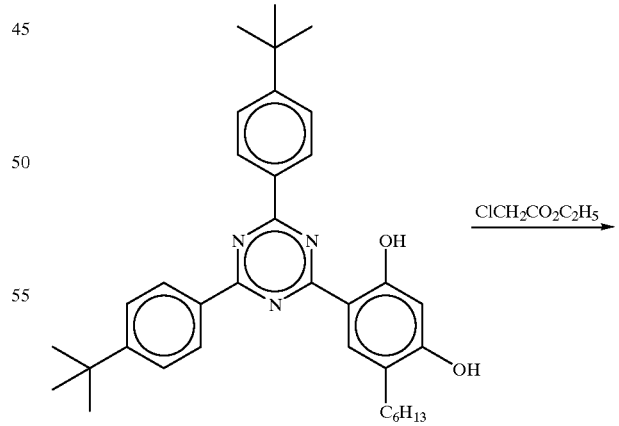

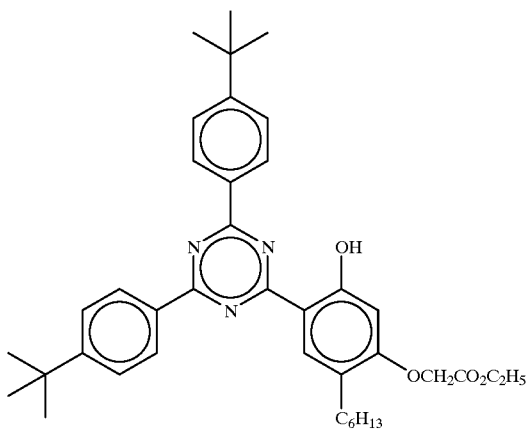

H

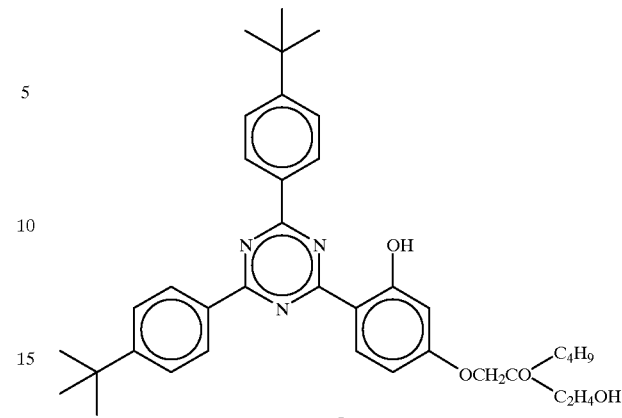

I

To a stirred mixture of 10 g of 2,4-bis(4-tert-butylphenyl)-6-(2,4-dihydroxy-5-hexylphenyl)-1,3,5-triazine, 7.4 g of anhydrous potassium carbonate, 0.5 g of potassium iodide, and 80 mL of acetone was added 2.2 mL (2.5 g) of ethyl chloroacetate. The mixture was stirred at reflux for 2.5 h and then allowed to cool to room temperature. The solids were removed by filtration and washed with methylene chloride. The combined filtrates were concentrated under reduced pressure to a volume of 75 mL and diluted with 50 mL of methanol. The resulting solid was collected by filtration and washed with methanol. After drying in vacuo, 10 g of 2,6-bis(4-tert-butylphenyl)-6-(2-hydroxy-4-ethoxycarbonylmethoxy-5-hexylphenyl)-1,3,5-triazine was obtained. The structure was verified by $^1$HNMR spectroscopy.

Example 9

Preparation of 2,4-bis(4-tert-butylphenyl)-6-[2-hydroxy-4-(N-(n-butyl)-N-(2-hydroxyethyl)methanamidooxy)phenyl]-1,3,5-triazine (Compound I)

A mixture of 6 g of 2,4-bis(4-tert-butylphenyl)-6-(2-hydroxy-4-ethoxycarbonylmethoxyphenyl)-1,3,5-triazine, 4 g of butyl ethanolamine, 0.13 g of 4-demethylaminopyridine, and 30 mL xylenes was stirred at reflux. After 8 hr, HPLC analysis (are % at 290 nm) showed complete conversion of starting material to one product. The mixture was allowed to cool and was concentrated under reduced pressure. The residue was crystallized from 100 mL of hexanes. The product was collected by filtration, washed with ice-cold hexanes, and dried in vacuo to give 7 g of 2,4-bis(4-tert-butylphenyl)-6-[2-hydroxy-4-(N-(n-butyl)-N-(2-hydroxyethyl)methanamidooxy)phenyl]-1,3,5-triazine as a pale yellow solid (>90% purity by HPLC). The structure was verified by $^1$HNMR spectroscopy.

Example 10

Preparation of 2,4-bis(4-tert-butylphenyl)-6-[2-hydroxy-4-(N-(n-butyl)-N-(2-hydroxyethyl)methanamidooxy-5-hexylpheynyl]-1,3,5-triazine (Compound J)

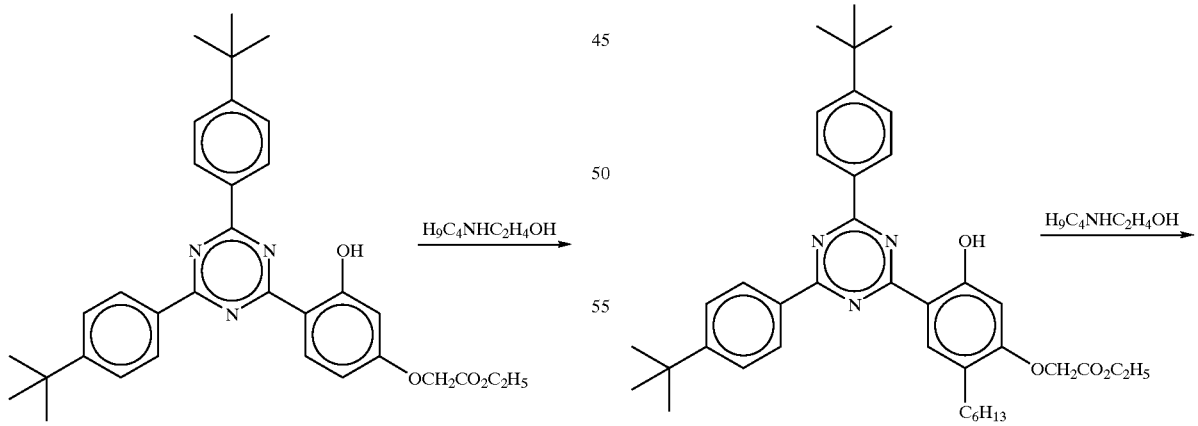

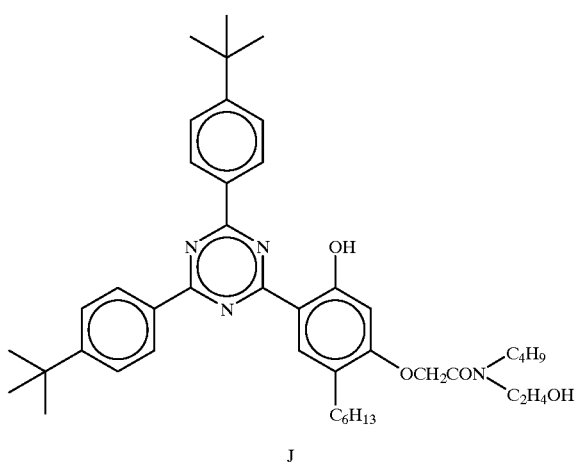

J

A mixture of 5 g of 2,4-bis(4-tert-butylphenyl)-6-(2-hydroxy-4-ethoxycarbonylmethoxy-5-hexylphenyl)-1,3,5-triazine, 4 g of butyl ethanolamine, 0.12 g of 4-dimethylaminopyridine, and 30 mL of xylenes was stirred at reflux. After 12 hr, HPLC analysis showed complete conversion of starting material to one product. The mixture was allowed to cool and was concentrated under reduced pressure. The residue was crystallized from 150 mL of hexanes. The product was collected by filtration, washed with ice-cold hexanes, and dried in vacuo to give 2,4-bis(4-tert-butylphenyl)-6-[2-hydroxy-4-(N-(n-butyl)-N-(2-hydroxyethyl)methanamidooxy)phenyl]-1,3,5-triazine as a pale yellow solid. The structure was verified by $^1$HNMR spectroscopy.

Example 12

Preparation of 2,4-bis(4-tert-butylphenyl)-6-(2,4-dihydroxyphenyl)-1,3,5-triazine 4-O-benzenesulfonate ester (Compound K)

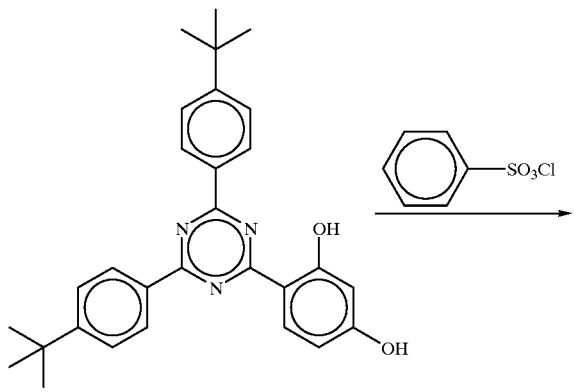

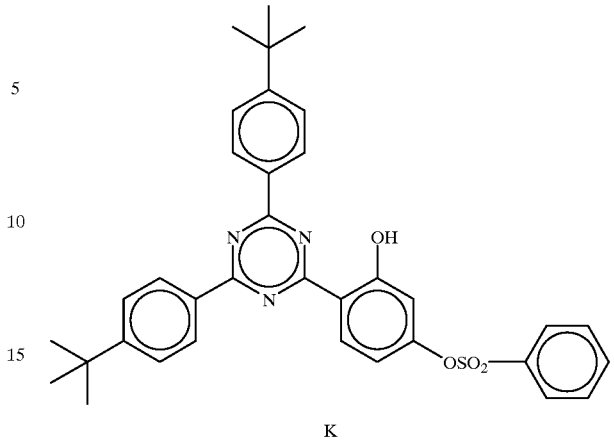

K

A stirred mixture of 12 g of 2,4-bis(4-tert-butylphenyl)-6-(2,4-dihydroxyphenyl)-1,3,5-triazine, 13.8 g of anhydrous potassium carbonate and 100 mL of tetrahydrofuran under nitrogen was cooled to 4° C. A solution of 4.1 mL (5.7 g) of benzenesulfonyl chloride in 20 mL of THF was added over 20 min. The resulting mixture was stirred at reflux for 32 hr. HPLC analysis showed complete conversion of starting material. The mixture was allowed to cool to room temperature and 10 mL of methanol was added. The mixture was filtered and concentrated under reduced pressure. The residue was triturated with 200 mL of hexanes and filtered, triturated with 250 mL of refluxing methanol, filtered hot, and washed with hot methanol. The solids were recrystallized from 200 mL of acetone/methanol (1:1 v/v), collected by filtration, washed with methanol, and dried in vacuo to give 8 g of 2,4-bis(4-tert-butylphenyl)-6-(2,4-dihydroxyphenyl)-1,3,5-triazine, 4-O-benzenesulfonate ester as a pale yellow solid. The structure was verified by $^1$HNMR spectroscopy.

Example A

Stabilized Polycarbonate Composition

Polycarbonate plaques are prepared as follows. GE Lexan 105 barefoot natural flake polycarbonate resin (melt temperature 310–333° C.) is dry blended with 0.35% stabilizer plus 0.10 wt % Mark® 2112 phosphite. The blended compositions are melt-mixed and extruded in a Haake torque rheometer equipped with a a 0.75-inch 25:1 single mixing screw extruder. The zone temperatures are 246, 265, 295, and 304° C. The extruded polycarbonate is pulled through a water bath, dried, pelletized, and redried at 120° C. for 4–48 hr in a forced air oven. The pellets are injection molded at 305–310° C. using an Arburg "Allrounder" hydraulic injection molder to form 2×2.5×0.100-inch plaques. The zone temperatures are: nozzle −305° C.; nozzle side −310° C.; middle −300° C.; and feed −290° C. The mold temperature is 100° C. Delta E data is obtained using a Macbeth Color Eye Colorimeter with illuminate C, 2° observer, specular component excluded, and UV component included.

The plaques are exposed in a xenon-arc WeatherOmeter following ASTM G-26 using Test Method B (Miami, Fla. conditions). The conditions are an irradiance of 0.35 W/m$^2$ at 340 nm, alternating cycles of light and darkness, intermittent water spray, and a black panel temperature of 63±3° C. Delta E (total color change) is measured after 400 hr. of exposure. Polycarbonate compositions containing the para-t-butyl Compound have less total color change than the unstabilized control composition.

Example B
Stabilized Coating Compositions

Stabilized clear acrylic melamine compositions are prepared and coated onto steel panels for accelerated weathering testing as follows. The para-tert-butyl compound (2% based on total resin solids) is pre-dissolved in xylenes, alone and in combination with Sanduvor® 3058 HALS (0.67% or 1.0% based on total resin solids), and added to the clear acrylic melamine formulation given in Table I. Steel panels pre-coated with ED5050A E-coat, 764204 primer, and 542DF716 white base-coat and measuring 4"×12" are obtained from ACT Laboratories, Inc. (Hillsdale, Mich.). The panels are coated with the clear coat formulations using the draw-down technique (WC-52 Wire-Cators™ obtained from Leneta Co., Ho-Ho-Kus, N.J.). The clear coats are allowed to flash for 10 min. at ambient temperature and cured for 30 min. at 135° C.

TABLE I

| Acrylic Melamine Clear Coat Formulation | |
| --- | --- |
| Material | Amount |
| Doresco ® TA 39-14 acrylic | 81.25 g |
| Cymel ® 303 cross-linker | 35.0 g |
| Cycat ® 4040 catalyst | 1.0 g |
| n-Butanol | 20.0 g |
| Xylene | 16.0 g |
| Product of Example 3[b] | 0.364 g[a] |

[a]Amount for 2% based on total resin solids
[b]2,4-bis(4-tert-butylphenyl)-6-(2-hydroxy-4-octyloxyphenyl)-1,3,5-triazine Accelerated weathering is carried out with a QUV following ASTM G53 (GM cycle), which is weathering under alternate cycles of (i) UV light at 70° C. for 8 hours and (ii) condensation with no UV light at 50° C. for 4 hr. Specular properties (gloss and distinctness of image, or DOI) are measured as a function of weathering time. Compositions containing 2% para-tert-butyl triazine have improved gloss and DOI retention relative to the unstabilized control. Compositions containing 1% HALS S-3058 in addition to para-tert-butyl triazine also exhibit improved gloss and DOI retention.

Example C
Stabilized Coating Compositions Containing 2,4-bis(4-tert-butylphenyl)-6-(2-acetoxy-4-octyloxyphenyl)-1,3,5-triazine Canadian patent application 2,162,645 has experimental data which shows that 2-acetoxy triazine UV absorbers improve the weatherability of acrylic melamine coating compositions. Weatherability is defined in terms of gloss retention. However no data on the yellowing behavior of these coating compositions was given. We have found that coating compositions containing 2-acetoxy triazines yellow upon exposure to UV light. We have further discovered that coating compositions containing the 2-(2-acetoxy-4-octyloxyphenyl)-4,6-bis-(4-tert-butylphenyl)-1,3,5-triazine yellow less than those containing 2-(2-acetoxy-4-hexyloxyphenyl)-4,6-diphenyl-1,3,5-triazine (Compound A12 of the cited patent).

The coating compositions were weathered using both UVB-313 bulbs (UV light intensity maximum at 313 nm) and UVA-340 bulbs (UV light intensity maximum of 340 nm). The results are summarized in Tables II and III. Under both weathering conditions, the t-Butyl compound surprisingly gave less yellowing. In the UVB-313 example, both equal weight (3.00%) and equimolar amounts (2.31%) of Compound A were evaluated. Even when compared against the lower, equimolar level of Compound A, the t-Butyl compound still afforded less yellowing.

TABLE II

YELLOWING PERFORMANCE OF STABILIZED COATING COMPOSITIONS UNDER QUV (UVB-313) WEATHERING

| | Hours QUV (UVB-313) Exposure | | | | | | |
| --- | --- | --- | --- | --- | --- | --- | --- |
| Compound F | 6 | 22 | 131 | 646 | 1180 | 1616 | 2000 |
| 3.0% t-Butyl[a] | 3.28 | 5.11 | 4.67 | 4.43 | 4.61 | 4.33 | 4.21 |
| 3.0% Compound L | 4.40 | 6.66 | 6.33 | 6.40 | 6.36 | 6.26 | 5.79 |
| 2.31% Compound L | 4.15 | 6.45 | 5.86 | 6.01 | 5.84 | 5.28 | 4.73 |

[a]2,4-bis(4-tert-butylphenyl)-6-(2-acetoxy-4-octyloxyphenyl)-1,3,5-triazine
Compound A is 2-(2-acetoxy-4-hexyloxyphenyl)-4,6-diphenyl-1,3,5-triazine

TABLE III

YELLOWING PERFORMANCE OF STABILIZED COATING COMPOSITIONS

UNDER QUV (UVA-340) WEATHERING

| | Hours QUV (UVB-340) Exposure | | | | | | |
| --- | --- | --- | --- | --- | --- | --- | --- |
| Compound F | 6 | 22 | 131 | 646 | 1180 | 1616 | 2000 |
| 3.0% t-Butyl[a] | 3.01 | 4.26 | 4.29 | 4.24 | 3.88 | 3.51 | 3.42 |
| 3.0% Compound L | 4.40 | 5.90 | 5.52 | 4.74 | 4.42 | 4.80 | 4.52 |

[a]2,4-bis(4-tert-butylphenyl)-6-(2-acetoxy-4-octyloxyphenyl)-1,3,5-triazine
Compound A is 2-(2-acetoxy-4-hexyloxyphenyl)-4,6-diphenyl-1,3,5-triazine Although the present invention is described with reference to certain preferred embodiments, it is apparent that modifications and variations thereof may be made by those skilled in the art without departing from the scope and spirit of this invention as defined by the appended claims.

What is claimed is:

1. A compound of formula (II) wherein:

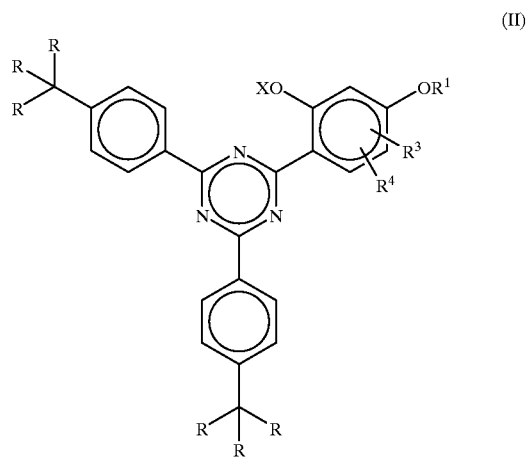

(II)

wherein X is hydrogen or a blocking group;
each R is independently a hydrocarbyl group of 1 to 21 carbon atoms;

$R^1$ is $C_1$–$C_{24}$ alkyl, $C_1$–$C_{24}$ branched alkyl, $C_2$–$C_{24}$ alkenyl, a cycloalkyl from 5–24 carbon atoms, an araalkyl from 7–24 carbon atoms, —$COR^9$, —$CO_2R^9$, —$CONHR^9$, —$SO_2R^9$, $C_1$–$C_{18}$ alkyl substituted with at least one hydroxy, $C_1$–$C_{18}$ alkoxy, $C_3$–$C_{18}$ alkenoxy, halogen, phenoxy, $C_1$–$C_{18}$ alkyl-substituted phenoxy, $C_1$–$C_{18}$ alkoxy-substituted phenoxy, halogen-substituted phenoxy, —COOH, —$COOR^9$, —$CONH_2$, —$CONHR^9$, —$CON(R^9)(R^{10})$, —$NH_2$, —$NHR^9$, —$N(R^9)(R^{10})$, —$NHCOR^{11}$, —$N(R^9)COR^{11}$, —$NHCOOR^{11}$, —$N(R^9)COOR^{11}$, —CN, —$OCOR^{11}$, —$OC(O)NHR^9$, —$OC(O)N(R^9)(R^{10})$, glycidyloxy, glycidyl, cyclohexyl optionally substituted with hydroxyl or —$OCOR^{11}$, and $C_2$–$C_{50}$ alkyl interrupted by at least one oxygen atom or carbonyl group and optionally substituted by one or more substituents selected from the group consisting of hydroxy or $C_1$–$C_{12}$ alkoxy;

wherein $R^9$ and $R^{10}$ independently of one another are $C_1$–$C_{12}$ alkyl, $C_3$–$C_{12}$ alkoxyalkyl, $C_4$–$C_{16}$ dialkylaminoalkyl, $C_5$–$C_{12}$ cycloalkyl, or $R^9$ and $R^{10}$ taken together are $C_3$–$C_9$ alkylene, $C_3$–$C_9$ oxoalkylene or $C_3$–$C_9$ azaalkylene; and $R^{11}$ is $C_1$–$C_{18}$ alkyl, $C_2$–$C_{18}$ alkenyl, or phenyl; and $R^3$ and $R^4$ are each hydrogen, hydrocarbyl group of 1 to 21 carbon atoms, halogen, hydroxyl, cyano, —O(hydrocarbyl), —O(functional hydrocarbyl), —N(hydrocarbyl)(hydrocarbyl) and mixtures thereof.

2. The compound according to claim 1, wherein at least two of the R groups are methyl and the other R group is methyl, ethyl, butyl, 2,2-dimethylpropyl, or phenyl.

3. The compound according to claim 2, wherein each R group is methyl.

4. The compound according to claim 1, wherein $R^1$ is selected from the group consisting of an alkyl of 1 to 24 carbon atoms optionally substituted by one or more hydroxyl, carboxyl, carboalkoxy, amide, epoxy or amino groups and optionally containing one or more carbonyl groups, oxygen atoms or nitrogen atoms in the chain;

an alkenyl of 2 to 24 carbon atoms optionally substituted by at least one hydroxyl, carboxyl, epoxy or amino group and optionally containing one or more carbonyl groups, oxygen or nitrogen atoms in the chain;

a cycloalkyl of 5 to 24 carbon atoms optionally substituted by at least one hydroxyl, carboxyl, or amino group and optionally containing carbonyl, oxygen, or nitrogen in the ring; and an aralkyl of 7 to 24 carbon atoms optionally substituted by at least one hydroxyl, carboxyl or amino group and may contain carbonyl, oxygen or nitrogen in the ring;

a polyoxyalkylene radical of the formula XII

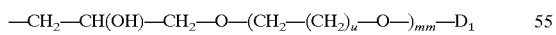

wherein $D_1$ is hydrogen, —$CH_2$—CH(OH)—$CH_2$—OH,

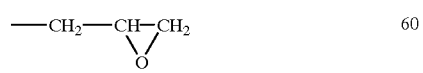

or $R^{25}$;

a polyoxyalkylene radical of the formula XIII

wherein $D_2$ is —$(CH_2)_u$—CO—$R^{22}$ or $R^{25}$;

a polyoxyalkylene radical of the formula VIII

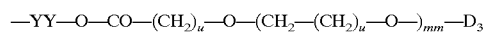

wherein $D_3$ is —$(CH_2)_u$—CO—$R^{22}$ or $R^{25}$;

a polyoxyalkylene radical of the formula XV

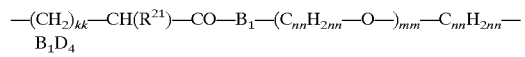

wherein $D_4$ is hydrogen of $R^{25}$;

a polyoxyalkylene radical of the formula XVI

wherein $D_5$ is —$NH_2$, —NH—$(CH_2)_2$—COO—$R^{23}$ or —O—$R^{25}$;

a polyoxyalkylene radical of the formula XVII

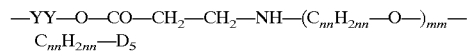

wherein $D_5$ is as defined under formula XVI;

a polyoxyalkylene radical of the formula XVIII

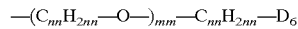

wherein $D_6$ is —NH—CO—$R^{24}$, —$OR^{25}$, OH or H;

a polyoxyalkylene radical of the formula XIX

wherein $D_7$ is —$OR^{25}$, —$NHCOR^{24}$ or —$OCH_2CH_2OR^{25}$;

$R^{21}$ is hydrogen or $C_1$–$C_{16}$ alkyl;

$R^{22}$ is halogen or —O—$R^{23}$;

$R^{23}$ is hydrogen, $C_1$–$C_6$ alkyl, $C_3$–$C_6$ alkenyl, aryl, or aryl-$C_1$–$C_4$-alkyl;

$R^{24}$ is hydrogen, $C_1$–$C_{12}$ alkyl or aryl;

$R^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl;

YY is unsubstituted or substituted $C_2$–$C_{20}$ alkylene;

$B_1$ is NH or O;

kk is zero or an integer from 1–16;

mm is an integer from 2 to 60;

nn is an integer from 2 to 6; and u is an integer from 1 to 4.

5. A compound of formula (III):

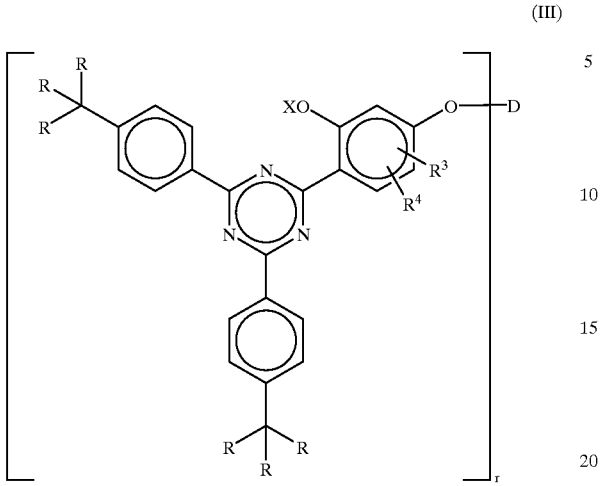
(III)

wherein

R, $R^3$, $R^4$, and X, are defined as in claim 1;

r is an integer between 2 and 4; and

D, when r is 2, is selected from the group consisting of $C_2$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$–$C_{20}$ alkyl which is interrupted by one or more oxygen atoms, —$CH_2CH(OH)CH_2O$—$R^{15}$—$OCH_2CH(OH)CH_2$—, —CO—$R^{16}$CO—, —CO—NH—$R^{17}$—NH—CO—, —$(CH_2)_s$—COO—$R^{18}$—OCO—$(CH_2)_s$— a polyoxyalkylene bridge member of the formula XX

—$CH_2$—$CH(OH)$—$CH_2O$—$(CH_2$—$(CH_2)_u$—O—$)_{mm}$—$CH_2$—$CH(OH)$—$CH_2$— (XX), a polyoxyalkylene bridge member of the formula XXI —CO—$(CH_2)_u$—O—$(CH_2$—$(CH_2)_u$—O—$)_{mm}$—$(CH_2)_u$—CO— (XXI), a polyoxyalkylene bridge member of the formula XXII —YY—O—$CO(CH_2)_u$—O—$(CH_2$—$(CH_2)_u$—O—$)_{mm}$—$(CH_2)_u$—COO—YY— (XXII), a polyoxyalkylene bridge member of the formula XXIII —$(CH_2)_{kk}$—$CH(R^{21})$—CO—$B_1(C_{nn}H_{2nn}$—O—$)_{mm}C_{nn}H_{2nn}$—$B_1$—CO—$CH(R^{21})$—$(CH_2)_{kk}$— (XXIII), a polyoxyalkylene bridge member of the formula XXIV —$COCH(R^{21})CH_2NH(C_{nn}H_{2nn}O)_{mm}C_{nn}H_{2nn}$—$NHCH_2$—$CH(R^{21})CO$— (XXIV)

a polyoxyalkylene bridge member of the formula XXV

—YY—O—CO—$(CH_2)_2$—NH—$(C_{nn}H_{2nn}$—O—$)_{mm}C_{nn}H_{2nn}$—NH—$(CH_2)_2COO$—YY— (XXV), a polyoxyalkylene bridge member of the formula XXVI —$(C_{nn}H_{2nn}$—O—$)_{mm}$—$C_{nn}H_{2nn}$— (XXVI), and a polyoxyalkylene bridge member of the formula XXVII —$CH(CH_3)$—$CH_2$—$(O$—$CH(CH_3)$—$CH_2)_a$—$(O$—$CH_2$—$CH_2)_b$—$(O$—$CH_2$—$CH(CH_3)_c$— (XXVII), wherein a+c=2.5 and b=8.5 to 40.5 or a+c=2 to 33 and b=0, $R^{21}$ is hydrogen or $C_1$–$C_{16}$ alkyl, $R^{22}$ is halogen or —O—$R^{23}$, $R^{23}$ is hydrogen, $C_1$–$C_6$ alkyl, $C_3$–$C_6$ alkenyl, aryl, or aryl-$C_1$–$C_4$-alkyl, $R^{24}$ is hydrogen, $C_1$–$C_{12}$ alkyl or aryl, $R^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl, $R^{26}$ is hydrogen or $C_1$–$C_4$ alkyl, $R^{27}$ is hydrogen, $C_1$–$C_{18}$ alkyl, $C_3$–$C_6$ alkenyl, $C_1$–$C_{18}$ alkoxy, halogen or aryl-$C_1$–$C_4$ alkyl, $R^{28}$ and $R^{29}$ independently of one another are hydrogen, $C_1$–$C_{18}$ alkyl, $C_3$–$C_6$ alkenyl, or $C_1$–$C_{18}$ alkoxy, or halogen;

$R^{30}$ is hydrogen, $C_1$–$C_4$ alkyl or CN,

YY is unsubstituted or substituted $C_2$–$C_{20}$ alkyl, $B_1$ is NH or O;

kk is zero or an integer from 1–16, mm is an integer from 2 to 60, nn is an integer from 2 to 6, u is an integer from 1 to 4, when r is 3, D is —$[(CH_2)_s$—$COO]_3$—$R^{19}$ and when r is 4, D is —$[(CH_2)_s$—$COO]_4$—$R^{20}$ wherein $R^{19}$ is $C_3$–$C_{10}$ alkanetriyl and $R^{20}$ is $C_4$–$C_{10}$ alkanetetryl; and s is 1–6;

$R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —$SO_2$—, —$CH_2$—, or —$C(CH_3)_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms.

6. A compound of formula (IV):

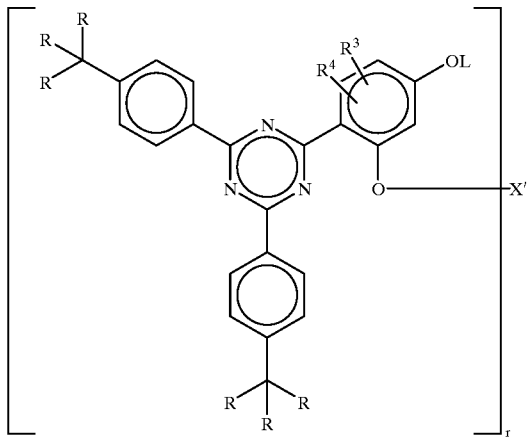

(IV)

wherein
R, $R^3$, and $R^4$, are defined as in claim 1;
L is hydrogen, $C_1$–$C_{24}$ alkyl, $C_1$–$C_{24}$ branched alkyl, $C_3$–$C_6$ alkenyl, —$COR^{12}$, —$COOR^{12}$, —$CONHR^{12}$, —$SO_2R^{13}$, $C_1$–$C_{18}$ alkyl which is substituted with at least one hydroxy, $C_1$–$C_{18}$ alkoxy, $C_3$–$C_{18}$ alkenoxy, halogen, phenoxy, $C_1$–$C_{18}$ alkyl-substituted phenoxy, $C_1$–$C_{18}$ alkoxy-substituted phenoxy, halogen-substituted phenoxy, —COOH, —$COOR^9$, —$CONH_2$, —$CONHR^9$, —$CON(R^9)(R^{10})$, —$NH_2$, —$NHR^9$, —$N(R^9)(R^{10})$, —$NHCOR^{11}$, —$N(R^9)COR^{11}$, —$NHCOOR^{11}$, —$N(R^9)COOR^{11}$, —CN, —$OCOR^{11}$, —$OC(O)NHR^9$, —$OC(O)N(R^9)(R^{10})$, glycidyloxy, glycidyl, cyclohexyl optionally substituted with hydroxyl or —$OCOR^{11}$ or $C_2$–$C_{50}$ alkyl optionally interrupted by at least one oxygen atom or carbonyl group and optionally substituted by at least one substituents selected from the group consisting of hydroxy and $C_1$–$C_{12}$ alkoxy,
wherein $R^9$ and $R^{10}$ independently of one another are $C_1$–$C_{12}$ alkyl, $C_3$–$C_{12}$ alkoxyalkyl, $C_4$–$C_{16}$ dialkylaminoalkyl, $C_5$–$C_{12}$ cycloalkyl, or $R^9$ and $R^{10}$ taken together are $C_3$–$C_9$ alkylene, $C_3$–$C_9$ oxoalkylene, $C_3$–$C_9$ azaalkylene;
$R^{11}$ is $C_1$–$C_{18}$ alkyl, $C_2$–$C_{18}$ alkenyl or phenyl;
$R^{12}$ is $C_1$–$C_{18}$ alkyl, $C_2$–$C_{18}$ alkenyl, phenyl, $C_1$–$C_{12}$ alkoxy, phenoxy, $C_1$–$C_{12}$ alkylamino, phenylamino, tolylamino or naphthylamino; and
$R^{13}$ is $C_1$–$C_{12}$ alkyl, phenyl, naphthyl or $C_7$–$C_{14}$ alkylphenyl;
r is an integer between 2 and 4; and
X', when r is 2, is selected from the group consisting of $C_2$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$–$C_{20}$ alkyl which is interrupted by one or more oxygen atoms, —$CH_2CH(OH)CH_2O$—$R^{15}$—$OCH_2CH(OH)CH_2$—, —CO—$R^{16}$—CO—, —CO—NH—$R^{17}$—NH—CO—, —$(CH_2)_s$—COO—$R^{18}$—OCO—$(CH_2)_s$—
a polyoxyalkylene bridge member of the formula XX —$CH_2$—CH(OH)—$CH_2$—O—$(CH_2$—$(CH_2)_u$—O—$)_{mm}$—$CH_2$—CH(OH)—$CH_2$— (XX), a polyoxyalkylene bridge member of the formula XXI —CO—$(CH_2)_u$—O—$(CH_2$—$(CH_2)_u$—O—$)_{mm}$—$(CH_2)_u$—CO— (XXI), a polyoxyalkylene bridge member of the formula XXII —YY—O—CO$(CH_2)_u$—O—$(CH_2$—$(CH_2)_u$—O—$)_{mm}$—$(CH_2)_u$—COO—YY— (XXII), a polyoxyalkylene bridge member of the formula XXIII —$(CH_2)_{kk}$—CH$(R^{21})$—CO—$B_1$—$(C_{nn}H_{2nn}$—O—$)_{mm}C_{nn}H_{2nn}$—$B_1$—CO—CH$(R^{21})$—$(CH_2)_{kk}$— (XXIII), a polyoxyalkylene bridge member of the formula XXIV —COCH$(R^{21})CH_2$NH$(C_{nn}H_{2nn}O)_{mm}C_{nn}H_{2nn}$—$NHCH_2$—CH$(R^{21})$CO— (XXIV), a polyoxyalkylene bridge member of the formula XXV —YY—O—CO—$(CH_2)_2$—NH—$(C_{nn}H_{2nn}$—O—$)_{mm}$—$C_{nn}H_{2nn}$—NH—$(CH_2)_2$COO—YY— (XXV), a polyoxyalkylene bridge member of the formula XXVI —$(C_{nn}H_{2nn}$—O—$)_{mm}$—$C_{nn}H_{2nn}$— (XXVI), and a polyoxyalkylene bridge member of the formula XXVII —CH$(CH_3)$—$CH_2$—(O—CH$(CH_3)$—$CH_2)_a$—(O—$CH_2$—$CH_2)_b$—(O—$CH_2$—CH$(CH_3))_c$— (XXVII), wherein a+c=2.5 and b=8.5 to 40.5 or a+c=2 to 33 and b=0,
$R^{21}$ is hydrogen or $C_1$–$C_{16}$ alkyl,
$R^{22}$ is halogen or —O—$R^{23}$,
$R^{23}$ is hydrogen, $C_1$–$C_6$ alkyl, $C_3$–$C_6$ alkenyl, aryl, or aryl-$C_1$–$C_4$-alkyl,
$R^{24}$ is hydrogen, $C_1$–$C_{12}$ alkyl or aryl,
$R^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl,
$R^{26}$ is hydrogen or $C_1$–$C_4$ alkyl,
$R^{27}$ is hydrogen, $C_1$–$C_{18}$ alkyl, $C_3$–$C_6$ alkenyl, $C_1$–$C_{18}$ alkoxy, halogen or aryl-$C_1$–$C_4$ alkyl,
$R^{28}$ and $R^{29}$ independently of one another are hydrogen, $C_1$–$C_{18}$ alkyl, $C_3$–$C_6$ alkenyl, or $C_1$–$C_{18}$ alkoxy, or halogen;
$R^{30}$ is hydrogen, $C_1$–$C_4$ alkyl or CN,
YY is unsubstituted or substituted $C_2$–$C_{20}$ alkyl,
$B_1$ is NH or O;
kk is zero or an integer from 1–16,
mm is an integer from 2 to 60,
nn is an integer from 2 to 6,
u is an integer from 1 to 4,
when r is 3, D is —$[(CH_2)_s$—COO$]_3$—$R^{19}$ and when r is 4, D is —$[(CH_2)_s$—COO$]_4$—$R^{20}$ wherein $R^{19}$ is $C_3$–$C_{10}$ alkanetriyl and $R^{20}$ is $C_4$–$C_{10}$ alkanetetryl; and
s is 1–6;

$R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —SO$_2$—, —CH$_2$—, or —C(CH$_3$)$_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms.

7. The compound of formula (V):

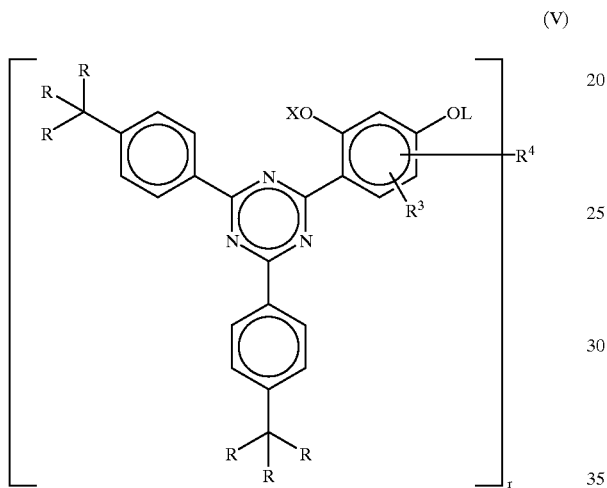

(V)

wherein

X, R, and $R^3$ are defined as in claim 1;

$R^4$ is selected from the group consisting of straight chain alkyl of 1 to 12 carbon atoms, branched chain alkyl of 1 to 12 carbon atoms, cycloalkyl of 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —SO$_2$—, —SO—E—SO—, —SO$_2$—E—SO$_2$—, —CH$_2$—NH—E—NH—CH$_2$—, and

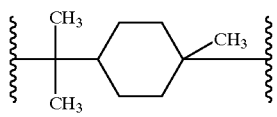

wherein E is selected from the group consisting of alkyl of 2 to 12 carbon atoms, cycloalkyl of 5 to 12 carbon atoms, alkyl interrupted by cyclohexyl of 8 to 12 carbon atoms, alkyl terminated by cyclohexyl of 8 to 12 carbon atoms;

r is an integer between 2 and 4; and

L is selected from a hydrogen, hydrocarbyl, halogen, hydroxyl, cyano, —O(hydrocarbyl), —O(functional hydrocarbyl), —N(hydrocarbyl)(hydrocarbyl), —N(functional hydrocarbyl)(functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups.

8. The compound according to claim 1, wherein $R^1$ is an alkyl group containing between 4 and 24 carbon atoms, X is hydrogen, each R is alkyl, and one of $R_3$ and $R_4$ is an alkyl group containing between 4 and about 24 carbon atoms while the other is hydrogen.

9. The compound according to claim 1, wherein $R^1$ is an alkyl group containing between 4 and 24 carbon atoms, X is hydrogen, each R is alkyl and $R_3$ and $R_4$ are hydrogen.

10. The compound according to claim 1, wherein X is independently selected from hydrogen and a blocking group and L is independently selected from —S(hydrocarbyl), —S(functional hydrocarbyl), —SO$_2$(hydrocarbyl), —SO$_3$(hydrocarbyl), —SO$_2$(functional hydrocarbyl), and —SO$_3$(functional hydrocarbyl).

* * * * *